(12) United States Patent
Reardon et al.

(10) Patent No.: US 10,024,797 B2
(45) Date of Patent: Jul. 17, 2018

(54) BIOSENSING SYSTEMS FOR MEASUREMENT OF LACTOSE

(75) Inventors: Kenneth F. Reardon, Fort Collins, CO (US); David S. Dandy, Fort Collins, CO (US); Ryan E. Holcomb, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 607 days.

(21) Appl. No.: 13/988,723

(22) PCT Filed: Nov. 22, 2011

(86) PCT No.: PCT/US2011/061956
§ 371 (c)(1),
(2), (4) Date: May 21, 2013

(87) PCT Pub. No.: WO2012/071471
PCT Pub. Date: May 31, 2012

(65) Prior Publication Data
US 2013/0244266 A1    Sep. 19, 2013

Related U.S. Application Data

(60) Provisional application No. 61/510,382, filed on Jul. 21, 2011, provisional application No. 61/415,920, filed on Nov. 22, 2010.

(51) Int. Cl.
*G01N 21/64* (2006.01)
*C12Q 1/32* (2006.01)
(Continued)

(52) U.S. Cl.
CPC ......... *G01N 21/6486* (2013.01); *C12Q 1/005* (2013.01); *G01N 21/7703* (2013.01); *G01N 21/6428* (2013.01); *G01N 2021/772* (2013.01); *G01N 2021/773* (2013.01); *G01N 2021/775* (2013.01); *G01N 2021/7786* (2013.01)

(58) Field of Classification Search
CPC ............ C12Q 1/005; G01N 2021/772; G01N 2021/773; G01N 2021/775; G01N 2021/7786; G01N 21/6486; G01N 21/7703
See application file for complete search history.

(56) References Cited

U.S. PATENT DOCUMENTS

| | | |
|---|---|---|
| 4,739,380 A | 4/1988 | Lauks et al. |
| 4,832,034 A | 5/1989 | Pizziconi et al. |

(Continued)

FOREIGN PATENT DOCUMENTS

| | | |
|---|---|---|
| EP | 277699 A2 | 10/1988 |
| EP | 1078248 B1 | 2/2001 |

(Continued)

OTHER PUBLICATIONS

Adachi, K., et al; Purification and properties of homogentisate oxygenase from Pseudomonas fluorescens. Biochim. Biophys. Acta 118 (1966) 88-97.

(Continued)

*Primary Examiner* — Christopher R Tate
*Assistant Examiner* — Aaron J Kosar
(74) *Attorney, Agent, or Firm* — Faegre Baker Daniels LLP

(57) ABSTRACT

Herein disclosed are biosensing systems that measure lactose concentration in a solution.

25 Claims, 9 Drawing Sheets

(51) Int. Cl.
*C12Q 1/00* (2006.01)
*G01N 21/77* (2006.01)

(56) References Cited

U.S. PATENT DOCUMENTS

| | | | |
|---|---|---|---|
| 4,848,906 | A | 7/1989 | Layton |
| 4,900,423 | A | 2/1990 | Iida et al. |
| 5,140,609 | A | 8/1992 | Jensen et al. |
| 5,141,312 | A | 8/1992 | Thompson et al. |
| 5,152,758 | A | 10/1992 | Kaetsu et al. |
| 5,156,810 | A | 10/1992 | Ribi |
| 5,177,012 | A | 1/1993 | Kim et al. |
| 5,250,439 | A | 10/1993 | Musho et al. |
| 5,340,722 | A | 8/1994 | Wolfbeis et al. |
| 5,462,879 | A | 10/1995 | Bentsen |
| 5,508,193 | A | 4/1996 | Mandelbaum et al. |
| 5,541,057 | A | 7/1996 | Bogart et al. |
| 5,543,317 | A | 8/1996 | Shields et al. |
| 5,580,527 | A | 12/1996 | Bell et al. |
| 5,629,214 | A | 5/1997 | Crosby |
| 5,698,083 | A | 12/1997 | Glass |
| 5,798,030 | A | 8/1998 | Raguse et al. |
| 5,837,196 | A | 11/1998 | Pinkel et al. |
| 5,837,454 | A | 11/1998 | Cozzette et al. |
| 5,853,669 | A | 12/1998 | Wolfbeis |
| 5,866,321 | A | 2/1999 | Matsue et al. |
| 5,972,199 | A | 10/1999 | Heller et al. |
| 5,972,638 | A | 10/1999 | Burlage et al. |
| 6,022,748 | A | 2/2000 | Charych et al. |
| 6,060,327 | A | 5/2000 | Keen |
| 6,100,080 | A | 8/2000 | Johansen |
| 6,136,979 | A | 10/2000 | Hudlicky et al. |
| 6,159,681 | A | 12/2000 | Zebala |
| 6,265,201 | B1 | 7/2001 | Wackett et al. |
| 6,271,015 | B1 | 8/2001 | Gilula |
| 6,284,522 | B1 | 9/2001 | Wackett et al. |
| 6,291,200 | B1 | 9/2001 | LeJeune et al. |
| 6,344,360 | B1 | 2/2002 | Colvin et al. |
| 6,369,299 | B1 | 4/2002 | Sadowsky et al. |
| 6,437,345 | B1 | 8/2002 | Bruno-Raimondi et al. |
| 6,576,449 | B2 | 6/2003 | Clark et al. |
| 6,592,746 | B1 | 7/2003 | Schmid-Schoenbein et al. |
| 6,766,183 | B2 | 7/2004 | Walsh et al. |
| 6,825,001 | B2 | 11/2004 | Wackett et al. |
| 6,927,246 | B2 | 8/2005 | Noronha et al. |
| 7,381,538 | B2 * | 6/2008 | Reardon .............. C12Q 1/002 435/23 |
| 7,595,181 | B2 | 9/2009 | Gruning et al. |
| 7,709,221 | B2 | 5/2010 | Rose et al. |
| 7,709,249 | B2 | 5/2010 | Bedingham et al. |
| 7,955,483 | B2 | 6/2011 | Gu et al. |
| 8,309,328 | B1 | 11/2012 | Dhawan et al. |
| 8,323,956 | B2 * | 12/2012 | Reardon .............. C12Q 1/002 435/177 |
| 8,622,900 | B2 | 1/2014 | Jain et al. |
| 8,622,901 | B2 | 1/2014 | Jain et al. |
| 9,493,805 | B2 | 11/2016 | Reardon |
| 9,493,806 | B2 | 11/2016 | Reardon |
| 9,499,853 | B2 | 11/2016 | Reardon |
| 9,796,998 | B2 | 10/2017 | Reardon et al. |
| 9,896,712 | B2 | 2/2018 | Reardon |
| 2002/0168733 | A1 | 11/2002 | Clark et al. |
| 2003/0207345 | A1 | 11/2003 | Arnold et al. |
| 2004/0265811 | A1 | 12/2004 | Reardon et al. |
| 2005/0084921 | A1 | 4/2005 | Cranley et al. |
| 2005/0221276 | A1 | 10/2005 | Rozakis et al. |
| 2006/0275855 | A1 | 12/2006 | Blackburn et al. |
| 2009/0026092 | A1 | 1/2009 | Reardon et al. |
| 2009/0078886 | A1 | 3/2009 | Schutzmann et al. |
| 2009/0221014 | A1 | 9/2009 | Reardon et al. |
| 2010/0116691 | A1 | 5/2010 | Papadimitrakopoulos |
| 2013/0065224 | A1 | 3/2013 | Lu et al. |
| 2014/0154724 | A1 * | 6/2014 | Reardon .............. C12Q 1/26 435/25 |
| 2014/0234882 | A1 * | 8/2014 | Reardon .............. C12Q 1/26 435/15 |
| 2015/0232913 | A1 * | 8/2015 | Reardon .............. C12Q 1/005 435/14 |
| 2017/0009270 | A1 | 1/2017 | Reardon et al. |
| 2017/0269001 | A9 | 9/2017 | Reardon et al. |

FOREIGN PATENT DOCUMENTS

| | | |
|---|---|---|
| EP | 1369687 A1 | 12/2003 |
| WO | WO 93/25892 | 12/1993 |
| WO | 99058963 A1 | 11/1999 |
| WO | WO03025627 A9 | 3/2003 |
| WO | 2004060297 A2 | 7/2004 |
| WO | 2009126841 A1 | 10/2009 |
| WO | 2014121850 A1 | 8/2014 |

OTHER PUBLICATIONS

Aldridge, W.N.; Serum esterases. I. Two types of esterase (A and B) hydrolysing p-nitrophenyl acetate, propionate and butyrate and a method for their determination. Biochem. J. 53 (1953) 110-117.

Amitai, G. et al.; Enhanced stereoselective hydrolysis of toxic organophosphates by directly evolved variants of mammalian serum paraoxonase; FEBS Journal 273 (2006) pp. 1906-1919.

Augusteyn, R.C., et al; On the homology of the active-site peptides of liver Carboxylesterases. Biochim. Biophys. Acta 171 (1969) 128-137.

Augustinsson, K.-B. and Heimburger, G. Enzymatic hydrolysis of organophosphorus compounds. I. Occurrence of enzymes hydrolysing dimethyl-amido-ethoxy-phosphoryl cyanide (Tabun). Acta Chem. Scand. 8 (1954) 753-761.

Bertoni, G., et al; "Cloning of the Genes for and Characterization of the Early Stages of Toluene and o-Xylene Catabolism in Pseudomonas stutzeri OX1," Applied and Environmental Microbiology, 1996, 62(10): pp. 3704-3711.

Bertoni, G., et al; "Analysis of the Gene Cluster Encoding Toluene/o-Xylene Monoxygenase from Pseudomonas stutzeri OX1," Applied and Environmental Microbiology, 1998. 64(10): pp. 3626-3632.

Buchinger, P.J. et al.; Characteristics of Microbial Assay for the Detection of Halogenated Hydrocarbons Using Cells of an Actinomycete-like Organism as a Biological Component; Acta Biotechnol. 17 (1997) 2, 123-130.

Byrne, A.M., et al; "Sequence Analysis of the Gene Cluster Encoding Toluene-3-monooxygenase from Pseudomonas pickettii PK01," Gene, 1995. 154: pp. 65-70.

Cardini, G. & Jurtshuk, P. The enzymatic hydroxylation of n-octane by *Corynebacterium* sp. strain 7E1C. J. Biol. Chem. 245 (1970) 2789-2796.

Cardy, D.L.N., V. Laidler, G.P.C. Salmond, and J.C. Murrell, "Molecular Analysis of the Methane Monooxygenase (MMO) Gene Cluster of Methylosinus trichosporium OB3b," Molecular Microbiology, 1991. 5(2): pp. 335-342.

Chang, K. H., et al; Isolation and characterization of the three polypeptide components of 4-chlorobenzoate dehalogenase from *Pseudomonas* sp. strain CBS-3. Biochemistry 31 (1992) 5605-5610.

Chopra, I. J. & Teco, G. N. C. Characteristics of inner ring (3 or 5) monodeiodination of 3,5-diiodothyronine in rat liver: evidence suggesting marked similarities of inner and outer ring deiodinases for iodothyronines. Endocrinology 110 (1982) 89-97.

Colby, J. et al; The soluble methane mono-oxygenase of Methylococcus capsulatus (Bath). Its ability to oxygenate n-alkanes, n-alkenes, ethers, and alicyclic, aromatic and heterocyclic compounds. Biochem. J. 165 (1977) 395-402.

Crooks, G. P. & Copley, S. D.; Purification and characterization of 4-chlorobenzoyl CoA dehalogenase from *Arthrobacter* sp. strain 4-CB1. Biochemistry, 33 (1994) 11645-11649.

de Souza, M. L. et al; Cloning, characterization, and expression of a gene region from *Pseudomonas* sp. strain ADP involved in the dechlorination of atrazine. Appl. Environ. Microbiol. 61 (1995) 3373-3378.

de Souza, M. L., et al; Atrazine chlorohydrolase from *Pseudomonas* sp. strain ADP: gene sequence, enzyme purification, and protein characterization. J. Bacteriol. 178 (1996) 4894-4900.

(56) References Cited

OTHER PUBLICATIONS

Dodgson, K.S., et al; Studies on sulphatases. 13. The hydrolysis of substituted phenyl sulphates by the arylsulphatase of Alcaligenes metacaligenes. Biochem. J. 64 (1956) 216-221.
Ensley, B.D. & Gibson, D.T. Naphthalene dioxygenase: purification and properties of a terminal oxygenase component. J. Bacteriol. 155 (1983) 505-511.
Fetzner, S., et al; Degradation of 2-chlorobenzoate by Pseudomonas cepacia 2CBS. Biol. Chem. Hoppe-Seyler 370 (1989) 1173-1182.
Fox, B.G., et al., "Methane Monooxygenase from Methylosinus trichosporium OB3b," Journal of Biological Chemistry, 1989. 264(17): pp. 10023-10033.
Fujisawa, H. & Hayaishi, O.; Protocatechuate 3,4-dioxygenase. I. Crystallization and characterization. J. Biol. Chem. 243 (1968) 2673-2681.
Goldman, P. & Milne, G. W. A.; Carbon-fluorine bond cleavage. II. Studies on the mechanism of the defluorination of fluoroacetate. J. Biol. Chem. 241 (1966) 5557-5559.
Goldman, P., et al.; Carbon-halogen bond cleavage. 3. Studies on bacterial halidohydrolases. J. Biol. Chem. 243 (1968) 428-434.
Goldman, P.; The enzymatic cleavage of the carbon-fluorine bond in fluoroacetate. J. Biol. Chem. 240 (1965) 3434-3438.
Goswami A., et al.; Inhibition by coumadin anticoagulants of enzymatic outer ring monodeiodination of iodothyronines. Biochem. Biophys. Res. Commun. 104 (1982) 1231-1238.
Hayaishi, O. & Sutton, W.B. Enzymatic oxygen fixation into acetate concomitant with the enzymatic decarboxylation of L-lactate. J. Am. Chem. Soc. 79 (1957) 4809-4810.
Heppel, L. A. & Porterfield, V. T. Enzymatic dehalogenation of certain brominated and chlorinated compounds. *J. Biol. Chem.* 176 (1948) 763-769.
Hosokawa, K. & Stanier, R.Y. Crystallization and properties of p-hydroxybenzoate hydroxylase from Pseudomonas putida. J. Biol. Chem. 241 (1966) 2453-2460.
Junker, F., et al; Dioxygenation and spontaneous deamination of 2-aminobenzene sulphonic acid in *Alcaligenes* sp. strain O-1 with subsequent meta ring cleavage and spontaneous desulphonation to 2-hydroxymuconic acid. Biochem. J. 300 (1994) 429-436.
Keuning, S., Janssen, D. B. & Witholt, B.; Purification and characterization of hydrolytic haloalkane dehalogenase from Xanthobacter autotrophicus GJ10; J. Bacteriol. 163 (1985) 635-639.
Kohler-Staub, D. & Leisinger, T.; Dichloromethane dehalogenase of Hyphomicrobium sp. strain DM2. J. Bacteriol. 162 (1985) 676-681.
Kumagai, H., et al; S-Carboxymethylcysteine synthase from Escherichia coli. Agric. Biol. Chem. 53 (1989) 2481-2487.
Lipke, H. & Kearns, C. W.; DDT dechlorinase. I. Isolation, chemical properties, and spectrophotometric assay. J. Biol. Chem. 234 (1959) 2123-2128.
Lipke, H. & Kearns, C. W.; DDT dechlorinase. II. Substrate and cofactor specificity. J. Biol. Chem. 234 (1959) 2129-2132.
McClay, K., B.G. Fox, and R.J. Steffan, "Chloroform Mineralization by Toluene-Oxidizing Bacteria," Applied and Environmental Microbiology, 1996. 62(8): pp. 2716-2722.
Moorefield, H. H. Purification of DDT-dehydrochlorinase from resistant houseflies. Contr. Boyce Thompson Inst. 18 (1956) 303-310.
Moriguchi, M., et al.; Dehalogenation and deamination of 1-2-amino-4-chloro-4-pentenoic acid by Proteus mirabilis. Agric. Biol. Chem. 51 (1987) 3295.
Motosugi, M., et al.; Preparation and properties of 2-halo acid dehalogenase from Pseudomonas putida. Agric. Biol. Chem. 46 (1982) 837-838.
Mulchandani, A. et al.; Biosensor for Direct Determination of Organophosphate Nerve Agents Using Recombatant *Escherichia coli* with Surface-Expressed Organophosphorus Hydrolase.—2. Fiber-Optic Microbial Bionsenor; ., Analytical Chemistry 1998 70 (23), 5042-5046.
Muller, C. et al.; Multicomponent fiberoptical biosensor for use in hemodialysis monitoring; SPIE Biomedical Fiber Optic Instrumentation; vol. 2131; pp. 555-562 (Jul. 1994).

Muller, R., et al.; Incorporation of [18O] water into 4-hydroxybenzoic acid in the reaction of 4-chlorobenzoate dehalogenase from *Pseudomonas* sp. CBS 3. Biochem. Biophys. Res. Commun. 124 (1984) 178-182.
Nagasawa, T.,et al.; Physiological comparison of D-cysteine desulfhydrase of *Escherichia coli* with 3-chloro-D-alanine dehydrochlorinase of Pseudomonas putida CR 1-1. Arch. Microbiol. 149 (1988) 413-416.
Nakagawa, H. and Takeda, Y. Phenol hydroxylase. Biochim. Biophys. Acta 62 (1962) 423-426.
Nordlund, I., et al, "Complete nucleotide sequence and polypeptide analysis of multicomponent phenol hydroxylase from Pseudomonas strain CF600," Journal of Bacteriology, 1990. 172: pp. 6826-6833.
PCT/US2002/017407 International Search Report; dated Sep. 24, 2003; 2 pages.
PCT/US2009/040121, International Search Report & Written Opinion dated Jul. 14, 2009, 7 Pages.
Pikus, J.D., et al; "Recombinant Toluene-4-Monoxygenase: Catalytic and Mossbauer Studies of the Purified Diiron and Rieski Components of a Four-Protein Complex," Biochemistry, 1996. 35: pp. 9106-9119.
Ramanathan, M. & Simonian, A.L.; Array biosensor based on enzyme kinetics monitoring by fluorescence spectroscopy: Application for neurotoxins detection; Biosensors and Bioelectronics 23 (2007) pp. 3001-3007.
Renganathan, V. Possible involvement of toluene-2,3-dioxygenase in defluorination of 3-fluoro-substituted benzenes by toluene-degrading *Pseudomonas* sp. strain T-12. Appl. Exp. Microbiol. 55 (1989) 330-334.
Rosenzwieg, A.C., et al. "Geometry of the Soluble Methane Monoxygenase Catalytic Diiron Center in Two Oxidation States," Chemistry and Biology, 1995. 2(6): pp. 409-418.
Schenk, T.,et al.; Enzymatic dehalogenation of pentachlorophenol by extracts from *Arthrobacter* sp. strain ATCC 33790. J. Bacteriol. 171 (1989) 5487-5491.
Scholtz, R., et al.; Characterization of 1-chlorohexane halidohydrolase, a dehalogenase of wide substrate range from an *Arthrobacter* sp. J. Bacteriol. 169 (1987) 5016-5021.
Simonian, AL, et al.; FET-Based Biosensors for the Direct Detection of Organophosphate Neurotoxins; Electroanalysis 2004; 16, No. 22; pp. 1896-1906.
Smallridge, R. C., et al. "3',5'-Diiodothyronine to 3'-monoiodothyronine conversion in the fed and fasted rat: enzyme characteristics and evidence for two distinct 5'-deiodinases" Endocrinology 108 (1981) 2336-2345.
Stainthorpe, A.C., et al., "The Methane Monooxygenase Gene Cluster of Methylococcus capsulatus (Bath)," Gene, 1990. 91: pp. 27-34.
Suzuki, K., Takemori, S. and Katagiri, M. Mechanism of the salicylate hydroxylase reaction. IV. Fluorimetric analysis of the complex formation. Biochim. Biophys. Acta 191 (1969) 77-85.
Yamada, H., et al; Synthesis of D-cysteine from 3- chloro-D-alanine and hydrogen sulfide by 3-chloro-D-alanine hydrogen chloride-lyase (deaminating) of Pseudomonas putida. Biochem. Biophys. Res. Commun. 100 (1981) 1104-1110.
Yen, K.-M., "Construction of Cloning Cartridges for Development of Expression Vectors in Gram-Negative Bacteria," J. Bacteriol., 1991. 173(17): pp. 5328-5335.
Yokota, T., et al.; Purification and properties of haloalkane dehalogenase from Corynebacterium sp. strain m15-3. J. Bacteriol. 169 (1987) 4049-4054.
Ziegler, D.M. and Pettit, F.H. Microsomal oxidases. I. The isolation and dialkylarylamine oxygenase activity of pork liver microsomes. Biochemistry 5 (1966) 2932-2938.
Conzuelo, F. et al., An Integrated amperometric biosensor for the determination of lactose in milk and dairy products, J. Agric. Food Chern., Jun. 23, 2010, pp. 7141-7148.
Jenkins, D.M. et al. Adaptation of a manometric biosensor to measure glucose and lactose, Biosensors Bioelectronics, Jan. 31, 2003, pp. 101-107.
Plata, M.R. et al., State-of-the-art of (bio)chemical sensor developments in analytical spanish groups, Sensors, Mar. 24, 2010, pp. 2511-2576.

(56) References Cited

OTHER PUBLICATIONS

PCT/US11/61956 International Search Report and Written Opinion dated Jun. 14, 2012, 10 pages.
PCT/US12/49384 International Search Report and Written Opinion dated Feb. 20, 2012, 11 pages.
PCT/US12/58331 International Search Report and Written Opinion dated Mar. 29, 2013, 11 pages.
PCT/US02/17407, International Preliminary Examination Report, dated Mar. 5, 2005, 4 pages.
Zhong, Z. et al., Fiber optic monooxygenase biosensor for toluene concentration measurement in aqueous samples, Biosensors and Bioelectronics 26 (2011) 2407-2412.
U.S. Appl. No. 10/478,822.
U.S. Appl. No. 12/100,308.
U.S. Appl. No. 12/358,140.
Mills, A. et al., Reversible, fluorescence-based optical sensor for hydrogen peroxide. Analyst 132 2007) 566-571.
Posch, H.E. & Wolfbeis. O.S., Optical sensor for hydrogen peroxide. Microchimica Acta 97 (1989) 41-50.
Rajendran, V., Lrudayaraj, J. Detection of glucose, galactose, and lactose in milk with a microdialysis-coupled flow injection amperometric sensor. J Dairy Sci. 85 (2002) 1357-61.
Pilloton, R et al., Lactose Determination in Raw Milk with a Two-Enzyme Based Electrochemical Sensor. Analytical Letters. 20 (1987) 1803-1814.
Tkác J, et al., Novel glucose non-interference biosensor for lactose detection based on galactose oxidase-peroxidase with and without co-immobilised beta-galactosidase. Analyst. 125 (2000) 1285-9.
Wichmann, R. & Vasic-Racki. D., Cofactor Regeneration at the Lab Scale. Adv Biochem Engin/Biotechnol 92 (2005) 225-260.
Zhao, H & van der Donk, W.A.. Regeneration of cofactors for use in biocatalysis. Current Opinion in Biotechnology. 14 (2003) 583-589.
Woodyer, R.D. et al. (2005) Regeneration of cofactors for enzyme biocatalysis. Enzyme Technology, 85-103.
Johannes, T.W. et al. (2005). Directed evolution of a thermostable phosphite dehydrogenase for NAD(P)H regeneration. Applied and Environmental Microbiology, 71(10), 5728-5734. doi:10.1128/AEM.71.10.5728-5734.2005.
Shaked, Z. & Whitesides, G.M., Enzyme-catalyzed organic synthesis: NADH regeneration by using formate dehydrogenase. J. Am. Chem. Soc. 102 (1980) 7104-7105.
Berríos-Rivera, .S.J. et al. Metabolic engineering of *Escherichia coli*: increase of NADH availability by overexpressing an NAD(+)-dependent formate dehydrogenase. Metab Eng. 4 (2002) 217-29.
Al-Raweshidy, H.S., et al. Electro-optic correlation in a spread spectrum multiplexing system for fibre optic interferometers, Optics Communications 81 Feb. 15, 1991, pp. 171-174.
U.S. Appl. No. 13/562,592 Non-Final Rejection dated Oct. 8, 2015, 20 pages.
Borisov, SM and Wolfbeis, OS "Optical Biosensors" Chem. Rev. 2008, 108, p. 423-461.
Carswell et al. "An Optical Oxygen Sensor Based on RUDPP Flourescent Quenching," SPIE vol. 2705, Mar. 25, 1996, pp. 22-30.
Chudobova, Ivana et al, "Fibre optic biosensor for the determination of D-glucose based on absorption changes of immobilized glucose oxidase," Analytica Chimica Acta, Issue 319 (1996) pp. 103-110.
Ferri, et al., "Review of Glucose Oxidases and Glucose Dehydrogenases: A Bird's Eye View of Glucose Sensing Enzymes," Journal of Diabetes Science and Technology, vol. 5, Issue 5 (Sep. 2011), pp. 1068-1076.
Godfrey, Larry "Choosing the Detector for your Unique Light Sensing Application" EG&G Optoelectronics Data Sheet, 1997, 6 pages.
Hollmann et al. "The First Synthetic Application of a Monooxygenase Employing Indirect Electrochemical NADH Regeneration," Chem Int. 2001. vol. 40 No. 1. pp. 169-171.
Issue Notification; May 14, 2008, for U.S. Appl. No. 10/478,822, 1 page.
Lee et al., "Proteome Changes after Metabolic Engineering to Enhance Aerobic Mineralization of cis-1, 2-Dichloreothylene," Journal of Proteome Research, 2006, pp. 1388-1397. American Chemical Society, Web.
Lipson, D. et al., Multifiber, Multiwavelength, Fiber Optic Flourescence Spectrophotometer, IEEE Trans. Biomed. Eng. vol. 39, No. 9 Sep. 1992, pp. 886-892.
Mars et al. "Effect of Trichloreothylene on Competitive Behavior of Toluene-Degrading Bacteria," Applied and Enviironmental Microbiology, 1998, vol. 64 (1), pp. 208-215.
Mars, et al., "Effect of Trichloroethylene on the Competitive Behavior of Toluene-Degrading Bacteria," Applied and Environmental Microbiology, vol. 64, No. 1 (Jan. 1998), pp. 208-215.
Mills, "Optical Oxygen Sensors, Utilising the Luminescence of Platinum Metals Complexes," Platinum Metals Review, vol. 41, Issue 3 (1997) pp. 115-127.
Moreno-Bondi, Maria C., et al., Oxygen Optrode for Use in a Fiber-Optic Glucose Biosensor, Analytical Chemistry, vol. 62, No. 21 (Nov. 1, 1990), pp. 2377-2380.
Neujahr, H.; Determination of Phenol and Catechol Concentrations with Oxygen Probes Coated with Immobilized Enzymes or Immobilized Cells; Applied Biochemistry and Biotechnology, 1982, 7:107-111.
Neujahr, Halina, "Determination of Phenol and Catechol Concentrations with Oxygen Probes Coated with Immobilized Enzymes or Immobilized Cells," Applied Biochemistry and Biotechnology, 1982, vol. 7, pp. 107-111.
Non-final Office Action issued in U.S. Appl. No. 12/100,308, dated Apr. 6, 2015, 9 pages.
Notice of Allowance dated Jan. 13, 2012, for U.S. Appl. No. 12/358,140, 7 pages.
Notice of Allowance dated Feb. 13, 2008, for U.S. Appl. No. 10/478,822, 3 pages.
Notice of Allowance dated Mar. 16, 2015, for U.S. Appl. No. 14/236,531, 7 pages.
Notice of Allowance dated Jun. 26, 2015, for U.S. Appl. No. 14/236,531, 7 pages.
Office Action issued in U.S. Appl. No. 14/348,426, dated Apr. 2, 2015, 19 pages.
Office Action dated Apr. 1, 2011, for U.S. Appl. No. 12/358,140, 8 pages.
Office Action dated Aug. 1, 2014, for U.S. Appl. No. 14/236,531, 16 pages.
Office Action dated Oct. 28, 2011, for U.S. Appl. No. 12/358,140, 9 pages.
Office Action dated Oct. 31, 2007, for U.S. Appl. No. 10/478,822, 6 pages.
Office Action dated May 17, 2007, for U.S. Appl. No. 10/478,822, 13 pages.
Peter, J. (1997). "Characteristics of a Microbial Assay for the Detection of Halogenated Hydrocarbons Using Cells of an Actinomycete-like Organism as a Biological Component." Acta Biotechnol. 17:(2). 123-130.
Response to Office Action filed Jan. 31, 2015, for U.S. Appl. No. 14/236,531, 14 pages.
Response to Office Action filed Aug. 1, 2011, for U.S. Appl. No. 12/358,140, 15 pages.
Response to Office Action filed Dec. 28, 2007, for U.S. Appl. No. 10/478,822, 10 pages.
Response to Office Action filed Dec. 28, 2011, for U.S. Appl. No. 12/358,140, 27 pages.
Response to Office Action filed Aug. 17, 2007, for U.S. Appl. No. 10/478,822, 79 pages.
Response to Restriction Requirement filed Feb. 12, 2007, for U.S. Appl. No. 10/478,822, 6 pages.
Restriction Requirement dated Jan. 12, 2007, for U.S. Appl. No. 10/478,822, 4 pages.
Rui et al. "Metabolic pathway engineering to enhance aerobic degradation of chlorinated ethenes and to reduce their toxicity by cloning a novel glutathione S-transferase, an evolved toluene o-monooxygenase, and y-glutamylcysteine synthetase," Environmental Microbiology, 2004, 6(5), pp. 491-500.

(56) References Cited

OTHER PUBLICATIONS

Schaffar, Bernhard P.H., et al., "A Fast Responding Fibre Optic Glucose Biosensor Based on an Oxygen Optrode," Biosensors & Bioelectronics, Issue 5 (1990), pp. 137-148.

Steiner, Mark-Steven, et al., "Optical methods for sensing glucose," Chemical Society Reviews, Issue 9 (Sep. 1, 2011), pp. 4805-4839.

Stokes et al. "An optical oxygen sensor and reaction vessel for high-pressure applications," Limnol. Ocearnogr., 1999, vol. 44(1):189-195.

Stokes et al. An optical oxygen sensor and reaction vessel for high-pressure applications, Limnol. Ocearnogr., 1999, 44(1):189-195.

Sundari, et al., "Retention of enzyme activity following freeze-drying the mycelium of ectomycorrhizal isolates: part II. Enzymes acting upon carbon compounds," World Journal of Microbiology and Biotechnology, vol. 16 (2000), pp. 865-868.

Trettnak, Wolfgang, et al., "A Fiberoptic Cholesterol Biosensor with an Oxygen Optrode as the Transducer," Analytical Biochemistry, Issue 184 (1990) pp. 124-127.

Trettnak, Wolfgang, et al., "Fibre Optic Glucose Biosensor With an Oxygen Optrode as the Transducer," Analyst, vol. 113 (Oct. 1988) pp. 1519-1523.

Trettnak, Wolfgang, et al., "Fibre-Optic Glucose Sensor with a pH Optrode as the Transducer," Biosensors, Issue 4 (1988), pp. 15-26.

van Beilen, et al., "Practical issues in the application of oxygenases," TRENDS in Biotechnology, vol. 21, No. 4, Apr. 2003, pp. 170-177.

Vilker, et al., "Challenges in Capturing Oxygenase Activity in Vitro," Journal of the American Oil Chemists' Society, vol. 76, No. 11 (1999), pp. 1283-1289.

Wilson, et al., "Glucose oxidase: an ideal enzyme," Biosensors & Bioelectronics, vol. 7 (1992), pp. 165-185.

Zakhari, S. "Overview: How is Alcohol Metabolized by the Body?" NIH-NIAAA archived online May 27, 2010, 12 pages.

Zhong, Z. "Fiber Optic Enzymatic Biosensors and Biosensor Arrays for Measurement of Chlorinated Ethenes," Dissertation, Colorado State University, (submission date Apr. 2, 2011), 158 Pages.

Mehrvar, et al., "Recent Developments, Characteristics, and Potential Applications of Electrochemical Biosensors," Analytical Sciences, vol. 20, Aug. 2004, pp. 1113-1126.

U.S. Appl. No. 14/348,426, filed Mar. 28, 2014 entitled Oxygenase-Based Biosensing Systems for Measurement of Halogenated Alkene Concentrations.

* cited by examiner

BIOSENSING SYSTEMS FOR MEASUREMENT OF LACTOSE

RELATED APPLICATIONS

This application claims the benefit of priority to U.S. Provisional Patent Application Ser. Nos. 61/415,920, filed Nov. 22, 2010, and 61/510,382, filed Jul. 21, 2011. Each of these applications is herein incorporated by reference.

GOVERNMENT RIGHTS

This invention was made with Government support under contract number BES-0529048 awarded by the National Science Foundation. The U.S. Government has certain rights in this invention.

BACKGROUND

Many different products in our daily diet are derived from milk. Milk contains sugar, fats and proteins. The primary sugar in milk is lactose. Lactose is found at levels of about 2-8 percent in milk. Lactose is a disaccharide sugar composed of galactose and glucose. In the dairy industry it is often necessary to measure lactose concentrations. For example, the production of lactose-free milk requires analysis of the lactose levels in the final product and could be optimized by lactose measurements during the process.

Analytical methods that are currently used to measure the concentration of lactose in milk take samples from the milk solutions and then send them to laboratories where they are analyzed. When the milk samples are removed, and during the time it takes to test these samples, the chemistry of the sample often changes and thus the test results may be inaccurate or inconsistent. Current analytical methods have a limited range of measurement because the response of their detection element saturates, returning the same signal for two different concentrations. In order to obtain an accurate concentration measurement under saturating conditions, the solution is diluted and then measured again. This can lead to measurement errors and is not readily suitable for continuous and in-situ measurements.

SUMMARY

The present instrumentalities advance the art and overcome the problems discussed above by providing biosensing systems, biosensing elements and methods for use in detecting one or more analytes such as lactose and hydrogen peroxide in milk, milk byproducts, or other solutions that may contain carbohydrate and/or hydrogen peroxide and also providing biosensing systems that allow measurements at high concentrations of an analyte and avoid sample dilution.

In one aspect, a biosensing system that measures lactose concentration in a solution is disclosed, wherein the biosensing system comprises an optode comprising an optical fiber having a first tip and a second tip, the first tip is covered by a luminescent transducer layer, the luminescent transducer layer is covered by a biocomponent layer, the biocomponent layer is covered by a porous membrane, the second tip is coupled to a photon-detection device, and the photon-detection device is coupled to a signal processing system.

In one embodiment, the biosensing system inter-relates the lactose concentration in the solution, the depth of the biocomponent layer, the depth of the porous membrane, the diffusion coefficient of the porous membrane, the $K_m$ and $V_{max}$ of the reaction between the biocomponent and lactose are selected such that Da is greater than the value of $1-\beta$ and the quotient between $Da^2$ and $4\beta$ is from about 10 to at least 1000, and $V_{max}$ is the maximum reaction rate achieved by the biocomponent layer under saturation lactose concentrations, and $K_m$ is the lactose concentration at which the reaction rate achieved by the biocomponent layer is half of $V_{max}$, and $\beta$ is the lactose concentration in the said solution divided by $K_M$ of said biocomponent for lactose, and $h_e$ is the thickness of the enzyme biocomponent layer which is embedded within a matrix, and $h_p$ is the thickness of a porous polymeric or ceramic material which sits atop the enzyme biocomponent layer, and $D_p$ is the diffusion coefficient of the polymer coating, and Da is a dimensionless number, and Da is $(h_e V_{max} h_p)/(D_p K_M)$.

In another embodiment, the biosensing system luminescent transducer layer contains a luminescent agent that is selected from the group consisting of a fluorescent agent, a phosphorescent agent, a bioluminescent agent, or a chemiluminescent agent.

In one embodiment, the biosensing system luminescent transducer layer contains a luminescent agent that is selected from the group consisting of trisodium 8-hydroxy-1,3,6-trisulphonate, fluoro(8-anilino-1-naphthalene sulphonate), tris(bipyridine)ruthenium(II) complex, RuDPP, ruthenium complexes, and acridinium- and quinidinium-based reagents, fluorescein, fluoresceinamine, or a fluorescein containing compound.

In one embodiment, the biosensing system biocomponent layer comprises a biocomponent selected from the group consisting of at least one enzyme selected from the group consisting of enzymes from Enzyme Commission numbers 1.1.3, 1.2.3, 1.3.3, 1.4.3, 1.5.3, 1.6.3, 1.7.3, 1.8.3, 1.9.3, 1.10.3, 1.16.3, 1.17.3, 1.21.3, and 3.2.1.23.

In one embodiment, the biosensing system biocomponent layer comprises a biocomponent displaced within a matrix comprising a hydrogel or other polymer, and wherein the hydrogel is selected from the group consisting of algal polysaccharides, agarose, alginate, gelatin, collagen, pectin, poly(carbamoyl)sulfonate, locust bean gum, and gellan, and wherein the other polymer is selected from the group consisting of polyacrylamide, polystyrene, polymethacrylate, polyvinylalcohol and polyurethane, and wherein the biocomponent is adsorbed within said matrix layer by physisorption or chemisorption.

In one embodiment, the biosensing system biocomponent is bound to the matrix layer through adding crosslinking agents to the biocomponent disposed within the matrix layer, and wherein the crosslinking agents are selected from the group consisting of glutaraldehyde, hexamethylene diisocyanate and 1,5-dinitro-2,4-difluorobenzene, glutaraldehyde, polyethyleneimine, hexamethylenediamine and formaldehyde.

In one embodiment, the biosensor luminescent transducer layer is bound in a layer of molecules bound to the first tip of the optical fiber, the layer of molecules is selected from the group consisting of cellulose, cellulose derivatives, silica, glass, dextran, starch, agarose, porous silica, chitin and chitosan.

In one embodiment, the biosensing system has a membrane that is polycarbonate having a pore size of from about 0.005 μm to about 0.025 μm.

In one embodiment, the biosensing system has a membrane that comprises a coating of polyurethane.

In one embodiment, the biosensing system biocomponent is beta-galactosidase and glucose oxidase and wherein said luminescent transducer layer interacts with oxygen.

In one embodiment, the biosensing system biocomponent is beta-galactosidase, glucose oxidase and catalase and wherein said luminescent transducer layer interacts with oxygen.

In one embodiment, the biosensing system biocomponent is beta-galactosidase and glucose oxidase and wherein said luminescent transducer layer interacts with protons.

In one embodiment, the biosensing system biocomponent is beta-galactosidase, glucose oxidase and catalase and wherein said luminescent transducer layer interacts with protons.

In one embodiment, the biosensing system biocomponent is beta-galactosidase and glucose oxidase and wherein said luminescent transducer layer interacts with oxygen and protons.

In one embodiment, the biosensing system biocomponent is beta-galactosidase, glucose oxidase and catalase and wherein said luminescent transducer layer interacts with oxygen and protons.

In one embodiment, the biosensing system biocomponent is beta-galactosidase and galactose oxidase and wherein said luminescent transducer layer interacts with oxygen.

In one embodiment, the biosensing system biocomponent is beta-galactosidase, galactose oxidase and catalase and wherein said luminescent transducer layer interacts with oxygen.

In one embodiment, the biosensing system biocomponent is beta-galactosidase and galactose oxidase and wherein said luminescent transducer layer interacts with protons.

In one embodiment, the biosensing system biocomponent is beta-galactosidase, galactose oxidase and catalase and wherein said luminescent transducer layer interacts with protons.

In one embodiment, the biosensing system biocomponent is beta-galactosidase and galactose oxidase and wherein said luminescent transducer layer interacts with oxygen and protons.

In one embodiment, the biosensing system biocomponent is beta-galactosidase, galactose oxidase and catalase and wherein said luminescent transducer layer interacts with oxygen and protons.

In one embodiment, the biosensing system biocomponent is carbohydrate oxidase and wherein said luminescent transducer layer interacts with oxygen.

In one embodiment, the biosensing system biocomponent is carbohydrate oxidase and catalase and wherein said luminescent transducer layer interacts with oxygen.

In one embodiment, the biosensing system biocomponent is carbohydrate oxidase and wherein said luminescent transducer layer interacts with protons.

In one embodiment, the biosensing system biocomponent is carbohydrate oxidase and catalase and wherein said luminescent transducer layer interacts with protons.

In one embodiment, the biosensing system biocomponent is carbohydrate oxidase and wherein said luminescent transducer layer interacts with oxygen and protons.

In one embodiment, the biosensing system biocomponent is carbohydrate oxidase and catalase and wherein said luminescent transducer layer interacts with oxygen and protons.

In one embodiment, the biosensing system biocomponent is cellobiose dehydrogenase and wherein said luminescent transducer layer interacts with protons.

In one aspect, a method of measuring the concentration of lactose in a solution is disclosed, the method comprises, communicating the interaction of a biocomponent with the lactose in the solution to a display and/or data storage device by communication means, the communication means comprising said biocomponent, lactose, oxygen and/or protons, a porous membrane, a biocomponent layer, a transducer layer, an optical fiber, a photon-detection device, a signal processor and said display and/or data storage device, the porous member separates the biocomponent layer from the solution, the biocomponent layer comprises the biocomponent displaced within a matrix, the biocomponent interacts with the lactose and either uses or generates oxygen and/or protons in the solution during the interaction, and the biocomponent layer is in contact with the transducer layer, and the transducer layer luminesces and wherein the luminescence is partially quenched by the oxygen and/or protons, and the luminescence is communicated to the photon-detection device through said optical fiber having a first end and a second end, the first end of the optical fiber is in contact and communicates with the transducer layer and the aid second end of the optical fiber is in contact and communicates with the signal processor, and the signal processor processes the communication from the luminescence of the transducer layer into a communication comprising the concentration of lactose in the solution, and the signal processor communicates the concentration of lactose in the solution to the display and/or data storage device.

In one embodiment, the method of measuring lactose concentration in the solution uses the following variables and the following algorithm in order to construct a biosensing system that measures lactose in the linear response range, the variables are the concentration of lactose in the solution, the depth of the biocomponent layer, the depth of the porous membrane, the diffusion coefficient of the porous membrane, the $K_m$ and $V_{max}$ of the reaction between the biocomponent and lactose are selected such that Da is greater than the value of 1–ß and the quotient between $Da^2$ and 4β is from about 10 to at least 1000, and wherein $V_{max}$ is the maximum reaction rate achieved by the biocomponent layer under saturation lactose concentrations, and wherein $K_m$ is the lactose concentration at which the reaction rate achieved by the biocomponent layer is half of $V_{max}$, and wherein β is the lactose concentration in the said solution divided by $K_M$ of said biocomponent for lactose, and wherein $h_e$ is the thickness of the enzyme biocomponent layer which is embedded within a matrix, and wherein $h_p$ is the thickness of a porous polymeric or ceramic material which sits atop the enzyme biocomponent layer, and wherein $D_p$ is the diffusion coefficient of the polymer coating, and wherein Da is a dimensionless number, and wherein Da is $(h_e V_{max} h_p)/(D_p K_M)$.

In one aspect, a biosensing system that detects carbohydrates in a solution is disclosed wherein the biosensing system comprises a biocomponent and a transducer. In one embodiment, the biosensing system has a biocomponent that is selected from the group consisting of enzymes from Enzyme Commission numbers 1.1.3, 1.2.3, 1.3.3, 1.4.3, 1.5.3, 1.6.3, 1.7.3, 1.8.3, 1.9.3, 1.10.3, 1.16.3, 1.17.3, 1.21.3, and 3.2.1.23. In one embodiment, the biosensing system has a biocomponent that is catalase and at least one enzyme selected from the group consisting of Enzyme Commission numbers 1.1.3, 1.2.3, 1.3.3, 1.4.3, 1.5.3, 1.6.3, 1.7.3, 1.8.3, 1.9.3, 1.10.3, 1.16.3, 1.17.3, 1.21.3, and 3.2.1.23. In one embodiment, the biosensing system has a transducer that interacts with oxygen. In one embodiment, the biosensing system has a transducer that that interacts with protons. In one embodiment, the biosensing system has a transducer that interacts with oxygen and protons.

In one aspect, a biosensing system that detects carbohydrate in a solution is disclosed wherein the biosensing system comprises a biocomponent, and a transducer, and a photon-detection device, and a signal processing system. In one embodiment, the biosensing system has a biocomponent that is selected from the group consisting of enzymes from Enzyme Commission numbers 1.1.3, 1.2.3, 1.3.3, 1.4.3, 1.5.3, 1.6.3, 1.7.3, 1.8.3, 1.9.3, 1.10.3, 1.16.3, 1.17.3, 1.21.3, and 3.2.1.23. In one embodiment, the biosensing system has a biocomponent that is catalase and at least one enzyme selected from the group consisting of Enzyme Commission numbers 1.1.3, 1.2.3, 1.3.3, 1.4.3, 1.5.3, 1.6.3, 1.7.3, 1.8.3, 1.9.3, 1.10.3, 1.16.3, 1.17.3, 1.21.3, and 3.2.1.23. In one embodiment, the biosensing system has a transducer that interacts with oxygen. In one embodiment, the biosensing system has a transducer that interacts with protons. In one embodiment, the biosensing system has a transducer that interacts with oxygen and protons.

In an aspect, a biosensing system that detects lactose in a solution is disclosed wherein the biosensing system comprises a biocomponent, and a transducer, and a photon-detection device, and a signal processing system. In an embodiment, the biosensing system biocomponent is beta-galactosidase and glucose oxidase and the transducer interacts with oxygen. In an embodiment, the biosensing system biocomponent is beta-galactosidase, glucose oxidase and catalase and the transducer interacts with oxygen. In an embodiment, the biosensing system biocomponent is beta-galactosidase and glucose oxidase and the transducer interacts with protons. In an embodiment, the biosensing system biocomponent is beta-galactosidase, glucose oxidase and catalase and the transducer interacts with protons. In an embodiment, the biosensing system biocomponent is beta-galactosidase and glucose oxidase and the transducer interacts with oxygen and protons. In an embodiment, the biosensing system biocomponent is beta-galactosidase, glucose oxidase and catalase and the transducer interacts with oxygen and protons. In an embodiment, the biosensing system biocomponent is beta-galactosidase and galactose oxidase and the transducer interacts with oxygen. In an embodiment, the biosensing system biocomponent is beta-galactosidase, galactose oxidase and catalase and the transducer interacts with oxygen. In an embodiment, the biosensing system biocomponent is beta-galactosidase and galactose oxidase and the transducer interacts with protons. In an embodiment, the biosensing system biocomponent is beta-galactosidase, galactose oxidase and catalase and the transducer interacts with protons. In an embodiment, the biosensing system biocomponent is beta-galactosidase and galactose oxidase and the transducer interacts with oxygen and protons. In an embodiment, the biosensing system biocomponent is beta-galactosidase, galactose oxidase and catalase and the transducer interacts with oxygen and protons. In an embodiment, the biosensing system biocomponent is carbohydrate oxidase and the transducer interacts with oxygen. In an embodiment, the biosensing system biocomponent is carbohydrate oxidase and catalase and the transducer interacts with oxygen. In an embodiment, the biosensing system biocomponent is carbohydrate oxidase and the transducer interacts with protons. In an embodiment, the biosensing system biocomponent is carbohydrate oxidase and catalase and the transducer interacts with protons. In an embodiment, the biosensing system biocomponent is carbohydrate oxidase and the transducer interacts with oxygen and protons. In an embodiment, the biosensing system biocomponent is carbohydrate oxidase and catalase and the transducer interacts with oxygen and protons. In an embodiment, the biosensing system biocomponent is cellobiose dehydrogenase and the transducer interacts with protons.

In one aspect, a biosensing system that measures hydrogen peroxide in a solution is disclosed wherein the biosensing element comprises a biocomponent and a transducer. In an embodiment, the biosensing system biocomponent is catalase and the transducer interacts with oxygen.

In an aspect, a biosensing system that detects hydrogen peroxide in a solution is disclosed wherein the biosensing system comprises a biocomponent, and a transducer, and a photon-detection device, and a signal processing system. In an embodiment, the biosensing system biocomponent is catalase and the transducer interacts with oxygen.

In an aspect, a biosensing system that detects lactose and hydrogen peroxide in a solution is disclosed wherein the biosensing system comprises a biocomponent, and a transducer, and a photon-detection device, and a signal processing system. In one embodiment, the biosensing system biocomponent is cellobiose dehydrogenase and catalase and the transducer layer interacts with oxygen and protons.

In one aspect, a method of detecting carbohydrate in a solution involves placing a biosensing system into contact with a solution containing carbohydrate, wherein the biosensing system comprises a biocomponent that interacts with the carbohydrate to consume oxygen, and the biocomponent is in contact with a transducer that luminesces and whose luminescence is partially quenched with oxygen, and the transducer is in contact with an optical fiber or other optical device that transfers photons to a photon-detection device that thereby transfers the luminescent photons of the transducer to a photon detection device and a signal processing system that provides the value of the concentration of the carbohydrate in the solution. In one embodiment, the method uses a biocomponent comprising catalase and at least one enzyme selected from the group consisting of Enzyme Commission numbers 1.1.3, 1.2.3, 1.3.3, 1.4.3, 1.5.3, 1.6.3, 1.7.3, 1.8.3, 1.9.3, 1.10.3, 1.16.3, 1.17.3, 1.21.3, and 3.2.1.23. In another embodiment, the method uses a transducer that comprises a RuDPP-based oxygen optode. In one embodiment, the method uses a photon-detecting device that comprises an image sensor and a signal processing system that comprises a transimpedance amplifier whose output is coupled to a microprocessor whose output is coupled to a display that displays the concentration of the carbohydrate in the solution. In one embodiment, the biosensing element of a biosensing system that detects lactose and hydrogen peroxide in a solution comprises a first biocomponent that reacts with lactose and a second biocomponent that reacts with hydrogen peroxide, wherein the first biocomponent is one or more enzymes selected from the group consisting of beta-galactosidase, glucose oxidase, galactose oxidase, cellobiose dehydrogenase and carbohydrate oxidase, and wherein the second biocomponent is catalase, and wherein the first biocomponent and the second biocomponent are within the same cells, and wherein the cells are immobilized within a matrix, and wherein the matrix is in contact with a transducer layer. In one embodiment, the cells are alive. In one embodiment, the cells are dead. In one embodiment, the transducer layer is comprised of a first chemical transducer that interacts with oxygen and a second chemical transducer that interacts with protons.

In one aspect, the sensing element of a biosensing system that detects lactose and hydrogen peroxide in a solution is disclosed wherein the sensing element comprises a first biocomponent that reacts with lactose and a second biocomponent that reacts with hydrogen peroxide, and the first biocomponent is one or more enzymes selected from a group consisting of beta-galactosidase, glucose oxidase, galactose oxidase, cellobiose dehydrogenase and carbohydrate oxidase, and wherein the second biocomponent is catalase, and wherein the first biocomponent and the second biocomponent are immobilized within a matrix, and wherein the matrix is in contact with a transducer layer.

In one aspect, a method for detecting the concentration of lactose and hydrogen peroxide in a solution is disclosed wherein a first biosensing system detects the lactose concentration and a second biosensing system detects the hydrogen peroxide concentration.

DETAILED DESCRIPTION

Figure 1:
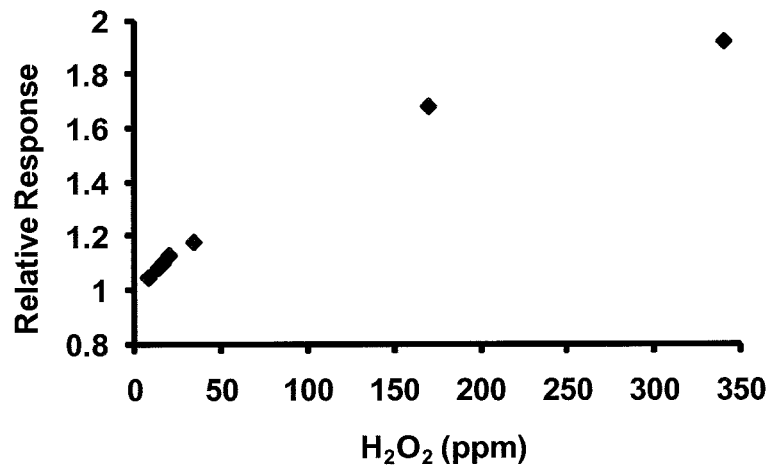
FIG. 1. Standard curve generated from hydrogen peroxide standards measured using a biosensing system. Signal change was measured relative to a blank solution of phosphate buffer having a pH of 7.2.

An analysis of lactose concentrations that is in-line with the processing of milk would save money and time involved in sending the samples to a lab for analysis while also allowing for the adjustment of processing the milk at the factory where the processing could easily be shifted towards another product or changed according to the reading of the lactose concentration of the milk.

A way to provide in-line analysis in a sample is to use a biosensing system. Biosensing systems offer the potential of measurements that are specific, continuous, rapid, and reagentless. Biosensing elements of biosensing systems combine a biocomponent which is coupled to a transducer to yield a device capable of measuring chemical concentrations. A biocomponent may be any biological detection agent. Examples of biocomponents include enzymes, whole cells, microorganisms, RNA, DNA, aptamers and antibodies. The biocomponent interacts with an analyte via a binding event and/or reaction. The role of the transducer is to convert the biocomponent detection event into a signal, usually optical or electrical. A transducer is typically a physical sensor such as an electrode, or a chemical sensor. The analyte normally interacts with the biocomponent through a chemical reaction or physical binding. For example, in the case of a biosensing system that uses an enzyme biocomponent, the enzyme biocomponent would react with the analyte of interest and a product or reactant of the enzyme catalyzed reaction such as oxygen, ammonia, hydrochloric acid or carbon dioxide, may be detected by an optical, electrochemical or other type of transducer.

Definitions

Biocomponent: A biocomponent binds, catalyzes a reaction of, or otherwise interacts with analytes, compounds, atoms or molecules. A biocomponent may refer to a single type or species of biocomponent or may refer to a mixture of multiple types or species of biocomponent. A biocomponent may alternatively be referred to in the plural form as biocomponents. Biocomponents may refer to multiple singular species of biocomponents or to multiple different types of species of biocomponents. Non-limiting examples of biocomponents include aptamers, DNA, RNA, proteins, enzymes, antibodies, cells, whole cells, tissues, single-celled microorganisms, and multicellular microorganisms. A biocomponent may be a cell or microorganism that has biocomponent enzymes within the cell or microorganism.

Analyte: An analyte is the substance or chemical constituent that is to be measured. In a reaction based biosensing system, the reaction of the analyte with a biocomponent causes a change in the concentration of a reactant or product that is measurable by the transducer. An analyte may also be a substrate of an enzyme. In other biosensing systems, the biocomponent may bind the analyte and not catalyze a reaction.

Transducer: A transducer is a device or compound which converts an input signal into an output signal of a different form. A transducer may convert a chemical input signal into an optical output signal, for example. A transducer may also be a device or compound that receives energy from one system and supplies energy of either the same or of a different kind to another system, in such a manner that the desired characteristics of the energy input appear at the output. In a reaction-based biosensing system, a transducer is a substance or device that interacts with the atoms, compounds, or molecules produced or used by the biocomponent. The interaction of the transducer with the atoms, compounds, or molecules produced or used by the biocomponent causes a signal to be generated by the transducer. The transducer may also generate a signal as an inherent property of the transducer. The signal may be an electrical current, a photon, a luminescence, or a switch in a physical configuration. In one embodiment, the signal produced by the transducer is quenched by a reactant or product of the biocomponent.

Optical transducer: An optical transducer is an optode that incorporates a luminescent reagent that luminesces. The luminescent reagent interacts with an atom, molecule, or compound and that interaction causes a change in the intensity and/or lifetime of the fluorescence of the optical transducer.

Physical transducer: A physical transducer is a device that interacts with an atom, molecule, photon or compound and that interaction causes a shift in its physical properties.

Biosensor: A biosensor measures compounds, atoms or molecules using a biocomponent. A biosensor may alternatively be referred to as a biosensing system and/or a biosensing element.

Biosensing system: A biosensing system contains a biosensing element, a photon-detection device, and a signal processing system. A biosensing system may alternatively be referred to as a biosensor system. Biosensing system may alternatively refer to various parts of the biosensing system such as the biosensing element, for example.

Biosensing element: A biosensing element detects analytes. A biosensing element comprises a biocomponent and a transducer. In certain embodiments, a biosensing element comprises a biocomponent, a transducer and/or an optode.

Crosslinking: Crosslinking is the process of linking polymeric molecules to one another. Crosslinking may be through chemical bonds or ionic interactions.

Matrix: A matrix is an interlacing, repeating cell, net-like or other structure that embodies the biocomponents. The immobilization material is an example of a matrix.

Immobilization material: Immobilization material is the substance, compound or other material used to immobilize the biocomponent onto the biosensing element transducer layer. The immobilization material may be a matrix or may be less ordered than a matrix.

Optode: An optode is an optical sensor device that optically measures a specific substance or quantity. An optode is one type of optical transducer. In one embodiment, for example, an optode requires a luminescent reagent, a polymer to immobilize the luminescent reagent and instrumentation such as a light source, detectors and other electronics. Optodes can apply various optical measurement schemes such as reflection, absorption, an evanescent wave, luminescence (for example fluorescence and phosphorescence), chemiluminescence, and surface plasmon resonance.

pH sensor: A pH sensor measures the concentration of hydrogen ions in a solution.

pH optode: A pH optode is an optode that has a detection element that interacts with hydrogen ions. An example of a detection element that interacts with hydrogen ions is, fluorescein, fluoresceinamine or other fluorescein containing compounds. In an embodiment, for example, a pH optode based on luminescence has a luminescent reagent that is pH responsive.

Luminescence: Luminescence is a general term which describes any process in which energy is emitted from a material at a different wavelength from that at which it is absorbed. Luminescence may be measured by intensity and/or by lifetime decay. Luminescence is an umbrella term covering fluorescence, phosphorescence, bioluminescence, chemoluminescence, electrochemiluminescence, crystalloluminescence, electroluminescence, cathodoluminescence, mechanoluminescence, triboluminescence, fractoluminescence, piezoluminescence, photoluminescence, radioluminescence, sonoluminescence, and thermoluminescence.

Fluorescence: Fluorescence is a luminescence phenomenon in which electron de-excitation occurs almost spontaneously, and in which emission from a luminescent substance ceases when the exciting source is removed. Fluorescence may be measured by intensity and/or by lifetime of the decay.

Phosphorescence: Phosphorescence is a luminescence phenomenon in which light is emitted by an atom or molecule that persists after the exciting source is removed. It is similar to fluorescence, but the species is excited to a metastable state from which a transition to the initial state is forbidden. Emission occurs when thermal energy raises the electron to a state from which it can de-excite. Phosphorescence may be measured by intensity and/or by lifetime of the decay.

Oxygen sensor: An oxygen sensor measures the concentration of oxygen in a solution.

Oxygen optode: An oxygen optode is an optode that has a detection element that interacts with oxygen. An example of a detection element that interacts with oxygen is Tris(4,7-diphenyl-1,10-phenanthroline)Ru(II) chloride, also known as RuDPP.

Photon-detection device: A photon-detection device is a class of detectors that multiply the current produced by incident light by as much as 100 million times in multiple dynode stages, enabling, for example, individual photons to be detected when the incident flux of light is very low. Photon-detection devices may be vacuum tubes, solid state photomultipliers or other devices that interact with incident light, and amplify or otherwise process the signal and/or photons produced by that interaction. Alternative embodiments of a photon-detection device include an image sensor, CCD sensors, CMOS sensors, photomultiplier tubes, charge coupled devices, photodiodes and avalanche photodiodes.

Signal processing system: A signal processing system processes the signal from a biosensing system into information that can be displayed to an end user. An example of a signal processing system is a converter or sampler device such as a signal processor or a transimpedance amplifier that accepts the output of a photon-detection device and in turn provides the input of a microprocessor that converts the signal into an output corresponding to the concentration of an analyte within the solution that was measured by the biosensing system. The output of the microprocessor is then communicated to an end user, for example by displaying the concentration on a screen.

Image sensor: An image sensor is a device that converts an optical image to an electric signal. Examples of image sensors include charge-coupled devices (CCD) or complementary metal-oxide-semiconductor (CMOS) active pixel sensors.

Sampler device: A sampler device reduces a continuous signal to a discrete signal. A common example is the conversion of a sound wave or light wave (a continuous signal) to a sequence of samples (a discrete-time signal).

Avalanche photodiode: An avalanche photodiode (APD) is a highly sensitive semiconductor electronic device that exploits the photoelectric effect to convert light to electricity. APDs can be thought of as photodetectors that provide a built-in first stage of gain through avalanche multiplication.

Converter: A converter is a current-to-voltage converter, and is alternatively referred to as a transimpedance amplifier. A converter is an electrical device that takes an electric current as an input signal and produces a corresponding voltage as an output signal. In another embodiment a converter may be a voltage-to-current converter.

Amperometric: Amperometric means to measure an electrical current.

Damköhler numbers (Da): Da are dimensionless numbers used to relate chemical reaction timescales to other phenomena occurring in a system. Da represents a dimensionless reaction time.

Michaelis-Menten equation: The Michaelis-Menten equation describes the rate of enzymatic reactions by relating reaction rate v to [S], the concentration of a substrate S. $V_{max}$ is the maximum rate achieved by the system, at maximum (saturating) substrate concentrations. The Michaelis constant $K_m$ is the substrate concentration at which the reaction rate is half of $V_{max}$. The equation is as follows:

$$v = \frac{V_{max}[S]}{K_m + [S]}.$$

Enzyme Commission number (EC number): The enzyme commission number is a nomenclature system used to classify enzymes by the reactions they catalyse. The recommendations of the Nomenclature Committee of the International Union of Biochemistry and Molecular Biology on the Nomenclature and Classification of Enzymes by the Reactions they Catalyse determine the EC number of an enzyme.

EC number 1.1.3: EC number 1.1.3 includes oxidoreductases that act on the CH—OH group of donors with oxygen as an acceptor such as: EC 1.1.3.3 malate oxidase, EC 1.1.3.4 glucose oxidase, EC 1.1.3.5 hexose oxidase, EC 1.1.3.6 cholesterol oxidase, EC 1.1.3.7 aryl-alcohol oxidase, EC 1.1.3.8 L-gulonolactone oxidase, EC 1.1.3.9 galactose oxidase, EC 1.1.3.10 pyranose oxidase, EC 1.1.3.11 L-sorbose oxidase, EC 1.1.3.12 pyridoxine 4-oxidase, EC 1.1.3.13 alcohol oxidase, EC 1.1.3.14 catechol oxidase (dimerizing), EC 1.1.3.15 (S)-2-hydroxy-acid oxidase, EC 1.1.3.16 ecdysone oxidase, EC 1.1.3.17 choline oxidase, EC 1.1.3.18 secondary-alcohol oxidase, EC 1.1.3.19 4-hydroxymandelate oxidase, EC 1.1.3.20 long-chain-alcohol oxidase, EC 1.1.3.21 glycerol-3-phosphate oxidase, EC 1.1.3.23 thiamin oxidase, EC 1.1.3.27 hydroxyphytanate oxidase, EC 1.1.3.28 nucleoside oxidase, EC 1.1.3.29 N-acylhexosamine oxidase, EC 1.1.3.30 polyvinyl-alcohol oxidase, EC 1.1.3.37 D-arabinono-1,4-lactone oxidase, EC 1.1.3.38 vanillyl-alcohol oxidase, EC 1.1.3.39 nucleoside oxidase ($H_2O_2$-forming), EC 1.1.3.40 D-mannitol oxidase, and EC 1.1.3.41 alditol oxidase.

EC number 1.2.3: EC number 1.2.3 includes oxidoreductases that act on the aldehyde or oxo group of donors with oxygen as an acceptor such as: EC 1.2.3.1 aldehyde oxidase, EC 1.2.3.3 pyruvate oxidase, EC 1.2.3.4 oxalate oxidase, EC 1.2.3.5 glyoxylate oxidase, EC 1.2.3.6 pyruvate oxidase (CoA-acetylating), EC 1.2.3.7 indole-3-acetaldehyde oxidase, EC 1.2.3.8 pyridoxal oxidase, EC 1.2.3.9 aryl-aldehyde oxidase, EC 1.2.3.11 retinal oxidase, EC 1.2.3.12 vanillate demethylase, EC 1.2.3.13 4-hydroxyphenylpyruvate oxidase, and EC 1.2.3.14 abscisic aldehyde oxidase.

EC number 1.3.3: EC number 1.3.3 includes oxidoreductases that act on the CH—CH group of donors with oxygen as an acceptor such as: EC 1.3.3.3 coproporphyrinogen oxidase, EC 1.3.3.4 protoporphyrinogen oxidase, EC 1.3.3.5 bilirubin oxidase, EC 1.3.3.6 acyl-CoA oxidase, EC 1.3.3.7 dihydrouracil oxidase, EC 1.3.3.8 tetrahydroberberine oxidase, EC 1.3.3.9 secologanin synthase, EC 1.3.3.10 tryptophan α,β-oxidase, EC 1.3.3.11 pyrroloquinoline-quinone synthase, and EC 1.3.3.12 L-galactonolactone oxidase.

EC number 1.4.3: EC number 1.4.3 includes oxidoreductases that act on the CH—$NH_2$ group of donors with oxygen as an acceptor such as: EC 1.4.3.1 D-aspartate oxidase, EC 1.4.3.2 L-amino-acid oxidase, EC 1.4.3.3 D-amino-acid oxidase, EC 1.4.3.4 amine oxidase, EC 1.4.3.5 pyridoxal 5'-phosphate synthase, EC 1.4.3.7 D-glutamate oxidase, EC 1.4.3.8 ethanolamine oxidase, EC 1.4.3.10 putrescine oxidase, EC 1.4.3.11 L-glutamate oxidase, EC 1.4.3.12 cyclohexylamine oxidase, EC 1.4.3.13 protein-lysine 6-oxidase, EC 1.4.3.14 L-lysine oxidase, EC 1.4.3.15 D-glutamate(D-aspartate) oxidase, EC 1.4.3.16 L-aspartate oxidase, EC 1.4.3.19 glycine oxidase, EC 1.4.3.20 L-lysine 6-oxidase, EC 1.4.3.21 primary-amine oxidase, EC 1.4.3.22 diamine oxidase, and EC 1.4.3.23 7-chloro-L-tryptophan oxidase.

EC number 1.5.3: EC number 1.5.3 includes oxidoreductases that act on the CH—NH group of donors with oxygen as an acceptor such as: EC 1.5.3.1 sarcosine oxidase, EC 1.5.3.2 N-methyl-L-amino-acid oxidase, EC 1.5.3.4 N6-methyl-lysine oxidase, EC 1.5.3.5 (S)-6-hydroxynicotine oxidase, EC 1.5.3.6 (R)-6-hydroxynicotine oxidase, EC 1.5.3.7 L-pipecolate oxidase, EC 1.5.3.10 dimethylglycine oxidase, EC 1.5.3.12 dihydrobenzophenanthridine oxidase, EC 1.5.3.13 N1-acetylpolyamine oxidase, EC 1.5.3.14 polyamine oxidase (propane-1,3-diamine-forming), EC 1.5.3.15 N8-acetylspermidine oxidase (propane-1,3-diamine-forming), EC 1.5.3.16 spermine oxidase, EC 1.5.3.17 non-specific polyamine oxidase, and EC 1.5.3.18 L-saccharopine oxidase.

EC number 1.6.3: EC number 1.6.3 includes oxidoreductases that act on NADH or NADPH with oxygen as an acceptor such as EC 1.6.3.1 NAD(P)H oxidase.

EC number 1.7.3: EC number 1.7.3 includes oxidoreductases that act on other nitrogenous compounds as donors with oxygen as an acceptor such as: EC 1.7.3.1 nitroalkane oxidase, EC 1.7.3.2 acetylindoxyl oxidase, EC 1.7.3.3 factor-independent urate hydroxylase, EC 1.7.3.4 hydroxylamine oxidase, and EC 1.7.3.5 3-aci-nitropropanoate oxidase.

EC number 1.8.3: EC number 1.8.3 includes oxidoreductases that act on a sulfur group of donors with oxygen as an acceptor such as: EC 1.8.3.1 sulfite oxidase, EC 1.8.3.2 thiol oxidase, EC 1.8.3.3 glutathione oxidase, EC 1.8.3.4 methanethiol oxidase, EC 1.8.3.5 prenylcysteine oxidase, and EC 1.8.3.6 farnesylcysteine lyase.

EC number 1.9.3: EC number 1.9.3 includes oxidoreductases that act on a heme group of donors with oxygen as an acceptor such as EC 1.9.3.1 cytochrome-c oxidase.

EC number 1.10.3: EC number 1.10.3 includes oxidoreductases that act on diphenols and related substances as donors with oxygen as an acceptor such as: EC 1.10.3.1 catechol oxidase, EC 1.10.3.2 laccase, EC 1.10.3.3 L-ascorbate oxidase, EC 1.10.3.4 o-aminophenol oxidase, EC 1.10.3.53-hydroxyanthranilate oxidase, EC 1.10.3.6 rifamycin-B oxidase, EC 1.10.3.9 photosystem II, EC 1.10.3.10 ubiquinol oxidase (H+-transporting), EC 1.10.3.11 ubiquinol oxidase, and EC 1.10.3.12 menaquinol oxidase (H+-transporting).

EC number 1.16.3: EC number 1.16.3 includes oxidoreductases that oxidize metal ions with oxygen as an acceptor such as EC 1.16.3.1 ferroxidase.

EC number 1.17.3: EC number 1.17.3 includes oxidoreductases that act on CH or $CH_2$ groups with oxygen as an acceptor such as: EC 1.17.3.1 pteridine oxidase, EC 1.17.3.2 xanthine oxidase, and EC 1.17.3.36-hydroxynicotinate dehydrogenase.

EC number 1.21.3: EC number 1.21.3 includes oxidoreductases that act on X—H and Y—H to form an X—Y bond with oxygen as an acceptor such as: EC 1.21.3.1 isopenicillin-N synthase, EC 1.21.3.2 columbamine oxidase, EC 1.21.3.3 reticuline oxidase, EC 1.21.3.4 sulochrin oxidase [(+)-bisdechlorogeodin-forming], EC 1.21.3.5 sulochrin oxidase [(−)-bisdechlorogeodin-forming], and EC 1.21.3.6 aureusidin synthase.

EC number 3.2.1.23: EC number 3.2.1.23 includes enzymes that are hydrolases, including glycosylases and glycosidases, i.e. enzymes hydrolysing O- and S-glycosyl compounds such as: EC 3.2.1.23 β-galactosidase.

Carbohydrate oxidase: Carbohydrate oxidases include enzymes classified under EC 1.1.3. Carbohydrate oxidase refers to oxidases that use at least oxygen and a carbohydrate as reactants. Non-limiting examples of carbohydrate oxidases include oxidases such as hexose oxidases which are capable of oxidizing several saccharides including glucose, galactose, maltose, cellobiose, and lactose. Additional examples of carbohydrate oxidases include monosaccharide oxidases, oligosaccharide oxidases and polysaccharide oxidases.

Advantages

Advantages in using biosensing systems for measuring analytes include fast measurement, generally on the order of minutes. This is a big advantage over traditional methods like GC or HPLC in which a lot of time is spent in collection of the sample and extraction of analytes from the sample.

Small size is another advantage of using biosensing systems. Biosensing systems and biosensing elements of the present disclosure have a compact design for field use and are therefore capable of measurements in confined places such as needles and catheters in vivo and in conditions where weight is critical like spacecraft or airplanes.

Another advantage of using biosensing systems is that they can be used to measure multiple analytes in a small sample in a continuous real-time measurement in a reversible manner with extremely low signal loss in an optical fiber as compared to electronic sensors such as amperometric assays. Furthermore, biosensing systems are capable of measuring at greater depths such as taking measurements in groundwater monitoring.

An advantage is the ability of biosensing systems to measure complex samples with no prior preparation of samples, no addition of the reagents in the samples. Biosensing systems can provide direct measurements in blood, food, and waste water, for example. This is important as removal of the sample from its environment (as in case of analyses by GC or HPLC) can change its chemistry and can thereby lead to inaccurate results. Also, this eliminates and simplifies sample separation steps and reduces the cost of the process. Measurements using biosensing systems can be made with minimum perturbations of the sample.

Biosensing systems have high specificity and sensitivity for measuring analytes of interest. Although traditional methods such as GC or HPLC may be very sensitive, they rely upon separating compounds before they are able to detect and identify the compounds. Other methods such as solid-phase enzyme immunoassay (ELISA) may be both sensitive and specific, but may not be as cost effective as a biosensing system, portable for field use or able to perform continuous, in-situ measurements.

Another advantage for using biosensing systems of the present disclosure is the low cost of mass production compared to most of the traditional methods like GC or HPLC. Biosensing systems of the present disclosure are easy to use compared to traditional measurement techniques such as gas chromatography, ion-chromatography and high-pressure liquid chromatography. Biosensing systems using the proper biocomponents can also measure the toxicity of chemicals whereas analytical methods such as GC and HPLC can only measure concentration.

Biocomponents

Biocomponents react with, bind to or otherwise interact with an analyte. Reactive biocomponents produce or react with atoms, molecules or compounds that interact with the transducer.

Enzymes are proteins that can serve as biocomponents that catalyze reactions with their substrates. Substrates may be analytes. The products or reactants of the enzymatic reactions are usually measured by the biosensing system. In one embodiment, the products of the substrates that react with the analyte may themselves be acted upon and thereby produce additional products which may be measured by the biosensing system. Therefore, a biosensing system may measure primary, secondary or even higher orders of products caused by an initial reaction or binding of the analyte with the biocomponent.

Generally, enzymes for use in biosensing systems may be disposed within whole cells or extracted from cells and purified. Whole cells and microorganisms are also biocomponents and are generally less expensive than purified enzymes and may provide an environment for longer enzyme stability. The cells and organisms used as biocomponents may or may not be living (able to replicate). Whether or not the cells are living, diffusion mechanisms and membrane-bound pumps may still be active that allow for the exchange of analytes and other compounds with the environment of the cell. It is often advantageous to use a dead cell or microorganism as a biocomponent at least because the proteolytic enzymes and pathways operating in a living cell generally cease to function and the enzymes, for example, that are responsible for binding or reacting with the analytes therefore last longer than they would in a living cell. Another advantage of using dead cells or microorganisms is that if the biosensing system is used in-situ, such as in-line testing of milk being produced at a factory, there can be no contamination of the sample with cells or microorganisms that may infect or adulterate the sample.

Purified enzymes may be used as a biocomponent in biosensing systems. Often, the extraction, isolation and purification of a particular enzyme can be expensive. Additionally, enzymes often lose their activity when separated from their intracellular environment that provides structural proteins, co-factors, consistent pH levels, buffers and other factors that contribute to the molecular integrity of the enzyme. Some enzymes are more robust than others. For example, enzymes isolated from extremophilic organisms such as hyperthermophiles, halophiles, and acidophiles often are more resistant to being exposed to environments substantially different from those found inside of a cell or microorganism. Extracellular enzymes are also usually more robust than enzymes that are membrane bound or solely exist within the cytosol.

An enzyme's resistance to becoming inactivated due to environmental factors, or even by the nature of the reaction that they catalyze, may be increased through mutagenic techniques. Such techniques are well known in the art and include various incarnations of changing the coding nucleotide sequence for the protein through various techniques. The proteins produced by expressing the mutagenic nucleotide sequences may then be tested for resistance to environmental factors and/or increased reactivity with substrates. Such an increase in reactivity may be due to advantageous binding specificity and/or increased kinetics of the binding and/or reaction catalyzed by the enzyme.

Methods of choosing cells and microorganisms that increase the response of the biosensing system may also be used to create biosensing systems that possess increased sensitivity, have quicker response times and last longer. Such techniques include directed evolution and using microassays to determine an increase in the production amount and/or rate of production of the molecules and/or atoms that react with the transducer layer.

Transducers

A transducer is a device or compound which converts an input signal into an output signal of a different form. A transducer may convert a chemical input signal into an optical output signal, for example. A transducer may also be a device or compound that receives energy from one system and supplies energy of either the same or of a different kind to another system, in such a manner that the desired characteristics of the energy input appear at the output. In a reaction-based biosensing system, a transducer is a substance or device that interacts with the atoms, compounds, or molecules produced or used by the biocomponent. The interaction of the transducer with the atoms, compounds, or molecules produced or used by the biocomponent causes a signal to be generated by the transducer. The transducer may also generate a signal as an inherent property of the transducer. The signal may be an electrical current, a photon, a luminescence, or a switch in a physical configuration. In one embodiment, the signal produced by the transducer is quenched by a reactant or product of the biocomponent. A transducer is a device that produces a measurable signal, or change in signal, upon a change in its chemical or physical environment. Transducers suited for biosensing systems that use enzymes as the biocomponent are those that interact with the reactants and/or products of the biocomponent and send a signal that is processed into a measurement reading. The nature of the interaction of the biological element with the analyte has a major impact on the choice of transduction technology. The intended use of the biosensing system imposes constraints on the choice of suitable transduction technique.

Amperometric transducers work by maintaining a constant potential on the working electrode with respect to a reference electrode, and the current generated by the oxidation or reduction of an electroactive species at the surface of the working electrode is measured. This transduction method has the advantage of having a linear response with a relatively simple and flexible design. Also, the reference electrode need not be drift-free to have a stable response. Since the signal generated is highly dependent on the mass transfer of the electroactive species to the electrode surface there can be a loss in sensitivity due to fouling by species that adsorb to the electrode surface. As a result of fouling, use of amperometric transducers is restricted where continuous monitoring is required. Enzymes, particularly oxidoreductases, are well suited to amperometric transduction as their catalytic activity is concerned with electron transfer.

Electroactive species that can be monitored at the electrode surface include substrates of a biological reaction (e.g., $O_2$, NADH), final products (e.g., hydrogen peroxide for oxidase reactions, benzoquinone for phenol oxidation) and also electrochemical mediators that can directly transfer electrons from the enzyme to the working electrode surface (e.g. hexacyanoferrate, ferrocene, methylene blue).

Potentiometric transducers work by having a potential difference between an active and a reference electrode that is measured under the zero current flow condition. The three most commonly used potentiometric devices are ion-selective electrodes (ISEs), gas-sensing electrodes and field-effect transistors (FETs). All these devices obey a logarithmic relationship between the potential difference and the activity of the ion of interest. This makes the sensors have a wide dynamic range. One disadvantage of this transducer is the requirement of an extremely stable reference electrode. Ion selective electrodes are commonly used in areas such as water monitoring. FETs are commercially attractive as they can be used to make miniaturized sensors, but manufacturing cost of FETs are high. Examples of potentiometric sensors are for acetaldehyde and cephalosporins, where the sensing electrode measures pH. Other examples are sensors used to measure creatinine, glutamine and nitrate with the sensing electrode detecting $NH_3$ gas.

Conductimetric transducers are often used to measure the salinity of marine environments. Conductance is measured by the application of an alternating current between two noble metal electrodes immersed in the solution. Due to specific enzyme reactions, they convert neutral substrates into charged products, causing a change in the conductance of the medium. This method can be used to make more selective and informative sensors by using multi-frequency techniques.

Optical transducers use optical phenomena to report the interaction of the biocomponent and the analyte. The main types of photometric behavior which have been exploited are ultraviolet and visible absorption, luminescence such as fluorescence and phosphorescence emission, bioluminescence, chemiluminescence, internal reflection spectroscopy using evanescent wave technology and laser light scattering methods.

One embodiment of an optical transducer uses luminescent reagents. In optical transducers that use luminescent reagents, a luminescent substance is excited by incident light, and as a result it emits light of longer wavelength. The intensity and/or lifetime decay of emitted light changes when an atom, molecule or compound binds or otherwise interacts with the luminescent substance. The atom, molecule or compound may be a reactant or product of the biocomponent. Thus, if a reactant or product of the biocomponent reacts with the luminescent transducer and affects the intensity and/or lifetime decay of the light emitted by the transducer layer, the change in the measurement of the intensity and/or lifetime decay can be measured as a response to a particular analyte. There are several luminescent reagents that may be useful as optical transducers. Examples include Tris(4,7-diphenyl-1,10-phenanthroline) Ru(II) chloride, also known as RuDPP, for oxygen sensors, trisodium 8-hydroxy-1,3,6-trisulphonate fluorescein, fluoresceinamine and other compounds containing fluorescein for pH sensors, fluoro(8-anilino-1-naphthalene sulphonate) for Na+ ion sensor and acridinium- and quinidinium-based reagents for halides.

Chemiluminescent and bioluminescent sensors work on principles similar to fluorescent sensors Chemiluminescence occurs by the oxidation of certain substances, usually with oxygen or hydrogen peroxide, to produce visible light. Bioluminescence is, for example, the mechanism by which light is produced by certain enzymes, such as luciferase.

Calorimetric transducers use the heat generated from biological reactions and correlate it with the reaction conditions. In order to measure such small amounts of heat liberated during the reaction, a very sensitive device is required. In the calorimetric technique a very sensitive, electrical resistance thermometer is used to detect temperature changes down to 0.001° C. This method is advantageous, as it is independent of the chemical properties of the sample. Calorimetric transduction has been used in a wide range of areas, including clinical chemistry, determination of enzyme activity, monitoring gel filtration, chromatography, process control and fermentation.

An acoustic transducer uses materials such as piezoelectrics as a sensor transducer due to their ability to generate and transmit acoustic waves in a frequency-dependent manner. The optimal resonant frequency for acoustic-wave transmission is highly dependent on the physical dimensions and properties of the piezoelectric crystal. Any change in the mass of the material at the surface of the crystal will cause quantifiable changes in the resonant frequency of the crystal. There are two types of mass-balance acoustic transducers: bulk wave and surface acoustic wave. Acoustic transduction is a relatively cheap technique but it has the disadvantage of having low sensitivity with non-specific binding. This technique is commonly used to measure the concentration of volatile gases and vapors. A piezoelectric immunobiosensor for measuring an analyte of interest in drinking water may use a piezoelectric crystal coated with polyclonal antibodies that bind to that analyte. When the analyte molecules come into contact with the antibodies, they bond with the antibodies causing a change in the crystal mass, which in turn leads to a shift in the oscillation frequency and produces a measurable signal that can be measured and correlated to the concentration of the analyte of interest within the sample.

Optical and Signal Processing Systems

In an embodiment, biosensing systems of the present disclosure have a biocomponent, a transducer, a photon-detection device, and a signal-processing system. A signal processing system processes the signal from a photon-detection device into information that can be displayed to an end user. An example of a signal processing system is a microprocessor that accepts an input signal from a photon-detection device that is coupled to a biosensing element. The signal processing system then uses a software program that encodes an algorithm. The algorithm used by the software transforms the data provided by the input signal and provides an output signal that correlates to a numerical display of the concentration of an analyte that the biosensing system detected.

In an embodiment of the present disclosure, a biosensing system comprises a biocomponent attached to a fiber optic pH optode, lens focusing system, photomultiplier (PMT), analog/digital (A/D) converter and a microprocessor. The biosensing system may contain a biosensing element that is coupled to a polymethylmethacrylate (PMMA) optical fiber optic. The length of this connecting optical fiber may vary from 1 mm to well over 1 km. In an embodiment, the other end of this cable is attached to a metal casing containing a 5 W halogen lamp or other light source and a lens focusing system. The light source should be able to operate at high temperatures, having a very short warm-up time in order to reach a constant power output. In one embodiment, light from the halogen lamp is first passed through a bandpass filter such as a 480-nm bandpass filter, for example. The light is then collected, paralleled and focused to the tip of fiber optic cable using a lens focusing system. An embodiment of the lens focusing system comprises spheric, aspheric, and convex lenses, and a dichroic mirror. Light from the lamp that radiates in opposite directions to the lens system may be refocused by the spheric lens and paralleled by the aspheric lens.

When light, for example light at 480 nm, is incident on a sensing tip coated with PVA/fluoresceinamine dye, fluorescence occurs. In an embodiment, this light is then passed back through a 520 nm bandpass filter or other bandpass filter having a frequency of light that is either blue or red shifted in comparison to the incident light wavelength, paralleled by focusing lens and then directed by the dichroic mirror onto the window of a single channel photo-detection device. The change in intensity and/or lifetime decay properties of the light can be measured. The photon detection device processes this light and the output potentiometric signal is sent to a computer interface using a connector block where it was converted into a digital signal by a data acquisition card. The final output is observed on a computer using software such as LabView software or other algorithmic software that interprets the signals from the sensing tip and processes them into correlating concentration measurements of the atom, compound, molecule or analyte of interest.

In one embodiment, the transducer of the biosensing element uses an evanescent wave to detect the luminescence of a reagent of the transducer. The evanescent wave could result from a carrier wave propagating within a planar waveguide or fiber optical cable. The carrier wave could be coupled to a photon-detection device that measures the interference of the evanescent wave with the carrier wave. This interference would correlate to the activity of the transducer and therefore the activity of the biocomponent and thus the concentration of an analyte of interest could be calculated from measuring the interference of the carrier wave within the planar waveguide.

Biosensing Elements

This disclosure embodies an optical enzymatic biosensing system for lactose and hydrogen peroxide. Several biosensing system designs are disclosed herein including biosensing elements on the tip of a fiber optical cable, and biosensing elements displaced upon a surface, for example. The biosensing system may be based on an optical pH or optical oxygen sensor. Carbohydrate oxidase may be used alone as the biocomponent or in conjunction with catalase. The biosensing elements may be separate from one another or combined into the same tip or biosensing element.

Some enzymes that react with lactose, such as carbohydrate oxidase, produce hydrogen peroxide as a by-product. In one embodiment, hydrogen peroxide can then be detected in the biosensing element and used as an indicator of the concentration of lactose in the aqueous solution. Some biosensing systems are made using food-grade enzymes and materials. These biosensing systems are advantageously used for measuring analytes in milk or other food products.

The disclosure presented herein is a set of biosensing system designs based on optical transduction. Optical enzymatic biosensing system designs using an optical signal transaction are more robust and less susceptible to chemical interference than electrochemical (e.g., amperometric) methods. In one embodiment, optical pH and optical oxygen sensors (optodes) employ fluorophores that are sensitive to either protons ($H^+$ ions) or molecular oxygen. Optical enzymatic biosensing elements are formed by combining a transducer and/or optode with a biocomponent that catalyzes a reaction with the analyte and results in altered pH or oxygen levels.

Hydrogen Peroxide as an Analyte

Hydrogen peroxide may be involved with, used, or produced in various processes in the dairy industry. Hydrogen peroxide is often used in food production to sterilize lines, including those carrying various foods and food ingredients. For example, lines that carry milk, processing vessels, and milk jugs are sterilized prior to filling to kill bacteria and prevent contamination of the fresh milk. Although hydrogen peroxide is not supposed to reach the consumer, sometimes the milk can arrive contaminated. Hydrogen peroxide has been shown to cause damage to the heart, lungs, arteries and veins upon ingestion. While the concentrations in milk are not likely to be fatal, the possibility of side effects still exists, and milk should be checked to ensure that it is safe to consume. This is particularly important since milk is a common drink for babies and small children.

Measuring Oxygen Generated by Catalase:

In one embodiment, catalase is used as a biocomponent coupled to an oxygen optode that measures a change in the concentration of oxygen in the solution. Catalase catalyzes the decomposition of hydrogen peroxide into water and oxygen. Thus, when hydrogen peroxide is in a solution and interacts with the biosensing element, oxygen is produced. The oxygen produced interacts with the transducer by quenching some of the luminescence of the transducer. Thus, the transducer produces a signal that is correlated to the concentration of oxygen in the sample which is related to the concentration of hydrogen peroxide.

Lactose as an Analyte

Several enzymes that react directly with lactose produce or consume an atom, molecule or compound that can be measured directly by the biosensing system are discussed herein. Additionally, several enzymes that react with at least one of the products of the initial reaction with lactose and create at least one product or use a reactant that interacts with the transducer layer of the biosensing element are discussed herein. Enzymes from several different enzyme commission number codes may be used as biocomponents in the biosensing systems and biosensing elements of the disclosures presented herein. Enzymes for use in the biosensing systems and biosensing elements disclosed herein may be selected from the group consisting of EC numbers, 1.1.3, 1.2.3, 1.3.3, 1.4.3, 1.5.3, 1.6.3, 1.7.3, 1.8.3, 1.9.3, 1.10.3, 1.16.3, 1.17.3, 1.21.3, and 3.2.1.23. Examples of embodiments of biosensing systems and biosensing elements for measuring lactose as an analyte include the following:

Measuring Use of Oxygen from Oxidation of Glucose:

Lactose can be a substrate for beta-galactosidase. Beta-galactosidase is an enzyme that hydrolyzes lactose into galactose and glucose. The glucose thereby generated may then be oxidized with glucose oxidase. When glucose oxidase reacts with glucose, hydrogen peroxide and a glucono lactone are generated. Using this scheme, oxygen is used and hydrogen peroxide is generated when lactose is present in a solution. The concentration of oxygen can be measured by an oxygen optode to detect oxygen consumption. Therefore, the concentration of lactose in a solution correlates to consumption of oxygen and the production of hydrogen peroxide.

In another embodiment, catalase may be added to the biosensing element. A benefit of this system is that the hydrogen peroxide generated by the action of the oxidase actually inhibits the catalysis of the oxidase through non-specific inhibition caused by the breakdown of hydrogen peroxide into hydroxyl radicals that react with amino acid moieties on the oxidase. In this embodiment, the catalase quickly degrades the hydrogen peroxide that is generated through the activity of the oxidase.

Measuring pH Changes Due to Glucono-Lactone Degradation:

In an embodiment of the above reactions of lactose, a biosensing system may use a pH optode to measure the pH change caused by the production of the hydrogen ions produced by the spontaneous hydrolysis of the D-glucono-1,5-lactone generated by the action of glucose oxidase on the glucose created by the reaction of lactose with beta-galactosidase.

In another embodiment, catalase may be added to the biosensing element. A benefit of this system is that the hydrogen peroxide generated by the action of the oxidase actually inhibits the catalysis of the oxidase through non-specific inhibition caused by the breakdown of hydrogen peroxide into hydroxyl radicals that react with amino acid moieties on the oxidase. In this embodiment, the catalase quickly degrades the hydrogen peroxide that is generated through the activity of the oxidase.

Measuring Use of Oxygen by the Oxidation of Galactose:

In another embodiment, cleavage of lactose with beta-galactosidase is followed by oxidation of the produced galactose with galactose oxidase in a reaction that uses oxygen and generates hydrogen peroxide. The concentration of oxygen can be measured by an oxygen optode to detect oxygen consumption. Therefore, the concentration of lactose in a solution correlates to the consumption of oxygen and the production of hydrogen peroxide.

In another embodiment, catalase may be added to the biosensing element. A benefit of this system is that the hydrogen peroxide generated by the action of the oxidase actually inhibits the catalysis of the oxidase through non-specific inhibition caused by the breakdown of hydrogen peroxide into hydroxyl radicals that react with amino acid moieties on the oxidase. In this embodiment, the catalase quickly degrades the hydrogen peroxide that is generated through the activity of the oxidase.

Measuring pH Changes Due to Galactono-Lactone Degradation:

In an embodiment of the above reactions of lactose, a biosensing system may use a pH optode to measure the pH change caused by the production of the hydrogen ions produced by the spontaneous hydrolysis of the D-galactono-1,5-lactone produced by the action of galactose oxidase on the galactose created by the reaction of lactose with beta-galactosidase.

In another embodiment, catalase may be added to the biosensing element. A benefit of this system is that the hydrogen peroxide generated by the action of the oxidase actually inhibits the catalysis of the oxidase through non-specific inhibition caused by the breakdown of hydrogen peroxide into hydroxyl radicals that react with amino acid moieties on the oxidase. In this embodiment, the catalase quickly degrades the hydrogen peroxide that is generated through the activity of the oxidase.

Measuring Oxygen Use by Carbohydrate Oxidase:

In an embodiment, carbohydrate oxidase oxidizes lactose while using oxygen to create a lactone and hydrogen peroxide. Thus, the use of oxygen is measured and correlated to the concentration of lactose in the solution. In another embodiment, the detection of the generation of hydrogen peroxide is correlated to the concentration of lactose in the solution either alone or in coordination with the detection of the use of oxygen.

In another embodiment, catalase may be added to the biosensing element. In this embodiment, the catalase quickly degrades the hydrogen peroxide that is generated through the activity of the oxidase.

Measuring pH Changes Due to δ-Lactone Degradation:

In an embodiment of the above reaction of lactose with carbohydrate oxidase, a biosensing system may use a pH optode to measure the pH change caused by the production of the hydrogen ions produced by lactobionic acid created from the spontaneous hydrolysis of the enzymatic product δ-lactone.

In another embodiment, catalase may be added to the biosensing element. A benefit of this system is that the hydrogen peroxide generated by the action of the oxidase actually inhibits the catalysis of the oxidase through non-specific inhibition caused by the breakdown of hydrogen peroxide into hydroxyl radicals that react with amino acid moieties on the oxidase. In this embodiment, the catalase quickly degrades the hydrogen peroxide that is generated through the activity of the oxidase.

Measuring Net Oxygen Consumption by Carbohydrate Oxidase and Catalase and Measuring pH Changes Due to the Degradation of the Lactone in the Same Biosensing Element:

In an embodiment, carbohydrate oxidase reacts with lactose to use oxygen and generate hydrogen peroxide, and the hydrogen peroxide generated then reacts with catalase to form water and oxygen. A benefit of this system is that the hydrogen peroxide generated by the action of carbohydrate oxidase actually inhibits the catalysis of carbohydrate oxidase through non-specific inhibition caused by the breakdown of hydrogen peroxide into hydroxyl radicals that react with amino acid moieties on carbohydrate oxidase. Thus, using this embodiment, the protons generated through the spontaneous degradation of the lactone change the pH of the solution. The measurement of the pH of the solution is therefore correlated to the concentration of lactose in the sample. One advantage of using this co-system of both carbohydrate oxidase and catalase is that the oxygen substrate is generated through the degradation of the inhibitory hydrogen peroxide. Thus, oxygen is recycled in the system and hydrogen peroxide is broken down before it can degrade carbohydrate oxidase.

Measuring pH from Cellobiose Dehydrogenase Activity:

In an embodiment, cellobiose dehydrogenase reacts with lactose and flavin adenine dinucleotide, reducing flavin adenine dinucleotide and oxidizing cellobiose into cellobiono-1,5-lactone and generating protons. The protons cause a change in the pH of the solution which is measured and correlated to the concentration of lactose in the solution.

Using a Carbohydrate Biosensing System and Hydrogen Peroxide Biosensing System in Tandem:

In yet another embodiment, a carbohydrate biosensing system and a hydrogen peroxide biosensing system may be used concurrently within the same sample but in different biosensing elements. In such an embodiment, hydrogen peroxide and carbohydrate concentrations are each measured by distinct biosensing elements or by a biosensing element that has both catalase and one or more of carbohydrate oxidase, beta-galactosidase, glucose oxidase, galactose oxidase, carbohydrate oxidase or cellobiose dehydrogenase.

As an example of an embodiment able to measure both pH and oxygen at the same time within the same biosensing system, catalase would react with hydrogen peroxide to produce oxygen which interacts with an oxygen-sensitive transducer layer on the biosensing element while cellobiose dehydrogenase reacts with lactose to produce a change in the pH of the solution which is measured by a pH-sensitive transducer layer on the same biosensing element. Thus one biosensing system simultaneously measures the concentrations of two different analytes that correlate to the concentrations of two different compounds of interest, here lactose and hydrogen peroxide.

Biosensing System Detection Range of Hydrogen Peroxide Biosensing Element

Biosensing systems were tested in the concentration range of 8-340 ppm $H_2O_2$ (340 ppm $H_2O_2$ is the same as 10 mM $H_2O_2$), see FIG. 1. This biosensing system gave a linear response from 8 to 170 ppm $H_2O_2$, with increasing but nonlinear response at higher concentrations of analyte.

In another example, the linear range of this biosensing system may be extended to about 60 mM by using a variety of different techniques to construct the biosensing element such as through various immobilization techniques and/or various cross-linking techniques.

Biosensing System Detection Range of Lactose Sensor

Figure 2:
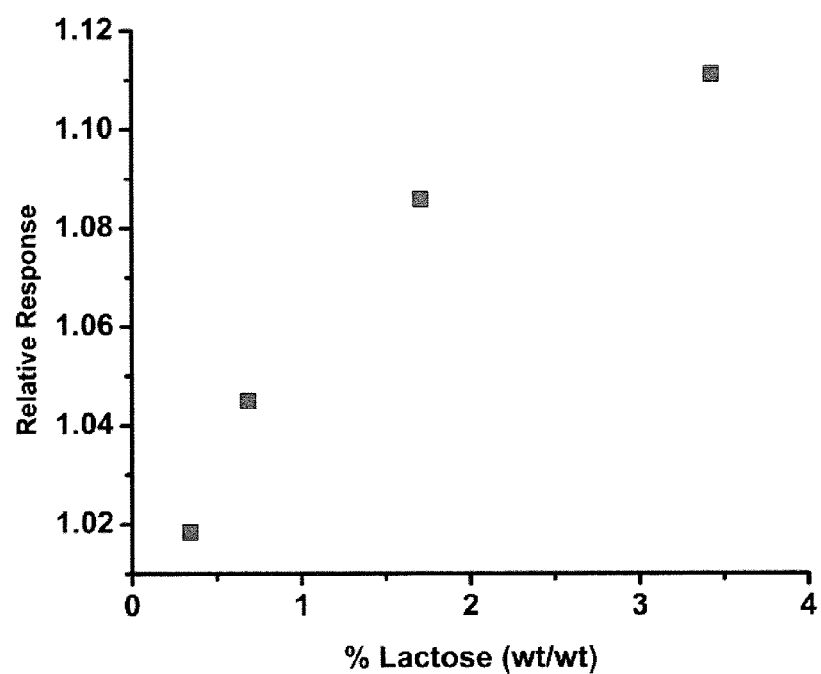
FIG. 2. Standard curve generated from lactose standards measured using a biosensing system. Signal change was measured relative to a blank solution of phosphate buffered saline (pH 7.4).

Biosensing systems were tested in the concentration range of 0.014-3.4% (wt/wt) lactose using biosensing elements and systems engineered for the lower and higher end of this concentration regime, respectively. Both lower concentration and higher concentration biosensing element types showed linear concentration dependence over specific concentration windows. The response of the higher concentration biosensing system is shown in FIG. 2. This particular biosensing system gave a linear response for lactose concentrations up to 1.7%, and had signal saturation for concentrations above this threshold.

In a prophetic example, the linear range of this biosensing system may be extended to at least 20% lactose by using a variety of different techniques to construct the biosensing system such as through various immobilization techniques and/or various cross-linking techniques.

Biosensing System Detection at High Analyte Concentrations

Some biosensing system applications may require the measurement of relatively high analyte concentrations, such as the measurement of lactose in milk (ca. 5% by weight, or 50 g/L) or ethanol content of beer (ca. 6% by weight, or 60 g/L). These concentrations are high enough to saturate the response of the biocomponent, meaning that all of the binding sites of an antibody or all of the enzymatic reaction sites are occupied. Under these saturating conditions, the biosensing system response is no longer dependent upon the analyte concentration and no measurement can be made.

One embodiment of the present disclosure is for biosensing systems that contain biosensing elements that use enzymes as biocomponents and can be used to provide a linear response in high analyte concentrations. Biosensing elements for the measurement of analytes at high concentrations can be used in many scenarios (such as the food and beverage examples listed above) and the concepts are broadly applicable for the measurement of other analytes in other solutions such as the measurement of halogenated hydrocarbons, for example.

Figure 7:
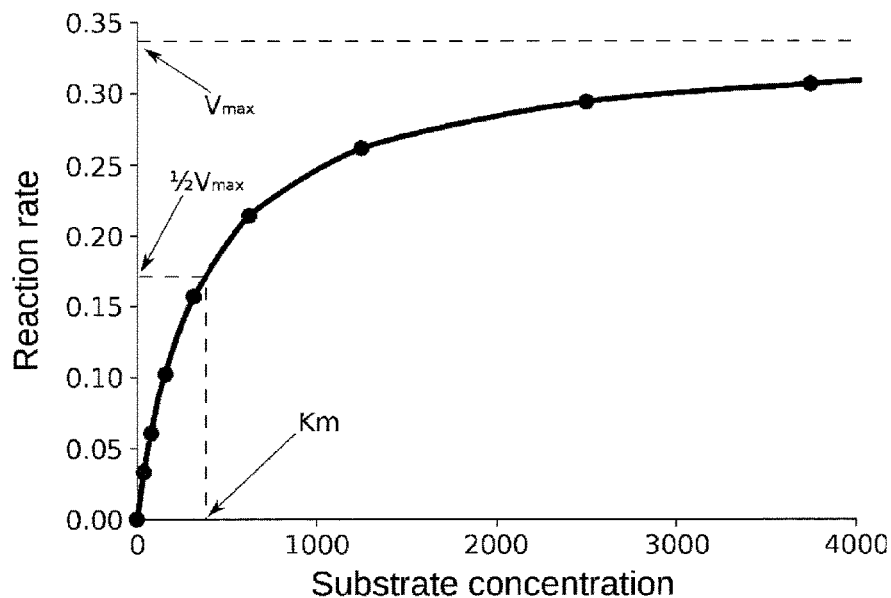
FIG. 7. Graphical representation of Michaelis-Menten equation relationships between enzyme reaction rate and substrate concentration. $K_m$ is the concentration of substrate at which the reaction rate is equal to ½ the reaction rate under saturating substrate conditions ($V_{max}$) of the enzymatic reaction.

Biosensing elements using enzymes as biocomponents may be constructed as thin enzyme-containing films deposited or placed over the transducer/fluorescent chemical layer. The response of biosensing systems that use these biosensing elements (signal as a function of analyte concentration) is governed by the rate of the enzymatic reaction and the manner in which that rate depends on the analyte concentration. For most enzymes, this relationship is the saturation type shown in FIG. 7 an modeled by the Michaelis-Menten equation in which the rate depends nearly linearly on analyte concentration at low concentrations but becomes independent of concentration at high concentrations. The Michaelis-Menten equation describes the rate of enzymatic reactions by relating reaction rate $v$ to [S], the concentration of a substrate S. $V_{max}$ is the maximum rate achieved by the system, at maximum (saturating) substrate concentrations. The Michaelis constant $K_m$ is the substrate concentration at which the reaction rate is half of $V_{max}$. The equation, equation 1, is as follows:

$$v = \frac{V_{max}[S]}{K_m + [S]}.$$

For biosensing element that has a thin-layer of enzyme biocomponent, this means that the biosensing element response becomes saturated and consequently it is not possible to distinguish one high concentration value from another.

To describe this high concentration range more accurately, it is convenient to use the Michaelis-Menten equation, which relates the enzymatic reaction rate $R_{enz}$ to the concentration of the analyte ($C_A$) as represented in the following equation, equation 2; $R_{enz}=kC_E C_A/K_M+C_A$ in which k and $K_M$ are parameters of the enzymatic reaction rate (depending on the enzyme and the analyte) and $C_E$ is the concentration of enzyme. The combined term $kC_E$ is frequently presented as $V_{max}$, the maximum reaction rate ("velocity"). The Michaelis-Menten equation has been found to accurately describe many different enzyme-catalyzed reactions.

When analyte concentrations are low enough that $C_A$ is much less than $K_M$, the Michaelis-Menten equation approximately reduces to a first-order (linear) dependence of the reaction rate on the analyte concentration, $R_{enz}=(V_{max}/K_M) C_A$ This linear response is the desired operating condition for a biosensing element. However, for biosensing elements that have a thin-layer of enzyme biocomponent, this range extends only to values of $C_A$ that are small relative to $K_M$; "small" can be interpreted as when $C_A$ is 10% or less of $K_M$. At higher analyte concentrations, the relationship of the enzymatic reaction rate to the analyte concentration, and thus the relationship of the biosensing element response to the analyte concentration, becomes increasingly nonlinear. Once the analyte concentration becomes much larger than $K_M$ such that $C_A+K_M=C_A$, the enzymatic reaction rate and the biosensing system response become essentially independent of $C_A$. Modifying the Michaelis-Menten equation for this case of $C_A \gg K_M$ yields $R_{enz}=V_{max}$.

The analysis above is based on the assumption that the analyte concentration in the vicinity of the enzyme molecules of the biocomponent layer ("local" concentration) is the same as in the solution in which the biosensing element is placed ("bulk solution" concentration). However, this situation can be manipulated such that the local concentration is lowered such that it falls within the linear measurement range. The local concentration can be related to the bulk solution concentration by either calculating the reaction-diffusion behavior of the system or through experimental calibration procedures.

A solution to extend the linear (useful) measurement range of biosensing elements that have an enzyme biocomponent beyond that available with thin-film designs is to add a mass transfer (diffusion) barrier. This diffusion barrier may take the form of a polymer coating, a membrane, or any other material through which the analyte passes more slowly than through the measurement medium. An effective diffusion barrier could also be created by increasing the thickness of the enzyme layer. Biosensing elements that have an increased thickness of the enzyme biocomponent layer are generally referred to as a thick-film biosensing element. Linear measurement ranges can be extended through the use of thick-film biosensing element designs. The rates of analyte mass transfer and reaction remain coupled in thick-film biosensing element designs. Thus, at some analyte concentration, the rate of mass transfer is high enough that the analyte concentration near the enzymes exceeds the linear reaction rate range and the biosensing system no longer has a direct, linear response to the analyte concentration.

In one embodiment, biosensing systems of the present disclosure use a design scheme for the construction of biosensing elements capable of measurements at high analyte concentrations. This is based on the combination of a high mass transfer resistance and a high biocomponent enzyme concentration, so that the analyte concentration near the transducer/fluorophore layer always remains in the linear reaction rate (and biosensing element response) range.

For any given concentration of any particular analyte, the appropriate ranges of the mass transfer coefficient of the analyte/substrate from the bulk solution to the enzyme biocomponent layer, and the reaction rate parameters of the enzyme layer, can be determined according to equation 3: $((Da+1-\beta)^2/4\beta) \gg 1$. Da is a dimensionless number used to relate chemical reaction timescales to other phenomena occurring in a system. Da represents a dimensionless reaction time. And where $\beta$=the substrate concentration in the bulk solution divided by $K_M$ of the enzyme for the substrate; and where Da is $(h_e V_{max} h_p)/(D_p K_M)$ where $h_e$ is the thickness of the enzyme biocomponent layer which is embedded within a matrix; $h_p$ is the thickness of a porous polymeric or ceramic material which sits atop the enzyme biocomponent layer; where $D_p$ is the diffusion coefficient of the polymer coating, see FIG. 8.

Figure 8:
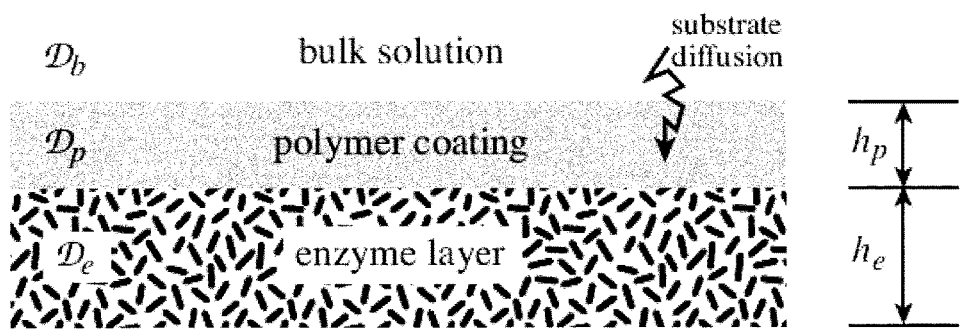
FIG. 8. Representation of enzymatic biosensing element for measuring analytes in high concentrations. $D_b$ is the diffusion coefficient of a substrate/analyte in the bulk solution; $D_p$ is the diffusion coefficient of a substrate/analyte in the polymer/ceramic coating; $D_e$ is the diffusion coefficient of a substrate/analyte in the enzyme layer which is embedded within a matrix; $h_p$ is the height of the polymer/ceramic coating; and $h_e$ is the height of the enzyme layer which is embedded within a matrix. The enzyme layer sits atop a transducer which may be part of an optode.

Therefore, by using equation 3, the calculations provide specific design parameters such as the thickness of the enzymatic biocomponent (detection) and mass transfer resistance layers such that a linear biosensing element and thus a linear biosensing system response is obtained for a given concentration, see FIG. 8.

In one embodiment of the present invention a method is used to provide the design parameters for constructing biosensing elements used in biosensing systems. The method uses a microprocessor that uses software encoding an algorithm that uses equation 3 to determine $h_e$, the thickness of the enzyme biocomponent layer which is embedded within a matrix; the thickness of a porous polymeric or ceramic material $h_p$, which sits atop the enzyme biocomponent layer; and a polymer coating that has the proper diffusion coefficient $D_p$, that can all be used to construct a biosensing element that has a linear response in a given range of analyte concentration in a solution.

The effect of having differing membrane materials placed upon the top of an enzyme biocomponent thin film are exemplified in the following embodiments of the biosensing elements and biosensing systems of the present disclosure.

In one embodiment, biosensing system A, biosensing element A has only a thin film of enzyme biocomponent that is immobilized on the surface of the biosensing element. In another embodiment, biosensing system B, biosensing element B has a porous membrane placed over the same thickness of enzyme biocomponent layer. In another embodiment, biosensing system C, the same thickness of enzyme biocomponent layer has a membrane layer placed over its biosensing element C that is less porous than the porous membrane of biosensing element B used in biosensing system B.

Biosensing elements B and C have a membrane material consisting of track-etched polycarbonate with a pore size of 0.015 µm. Additional mass transfer resistance was provided for biosensing element C by casting a polyurethane coating on top of the porous membrane material.

Figure 9:
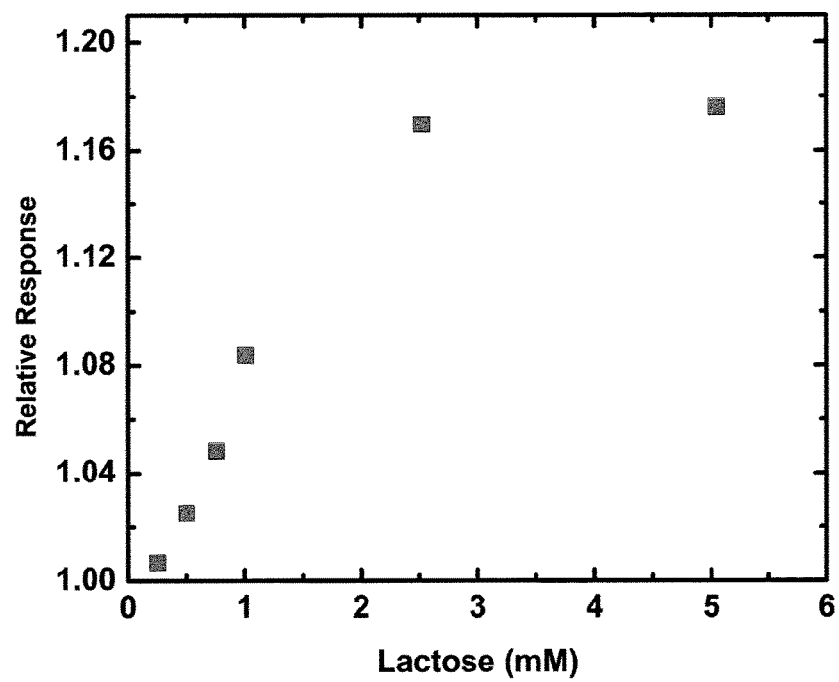
FIG. 9. Response curve for biosensing system A. Biosensing system A is a lactose sensor with a thin film of enzyme immobilized on the surface. Signal change was measured relative to a blank solution of phosphate buffered saline (pH 7.4).

The response of biosensing system A to a series of lactose standards is show in FIG. 9. From FIG. 9 it is seen that biosensing element A's response begins to saturate at concentrations above 1.01 mM lactose. Signal saturation is due to the presence of substrate/analyte at concentrations that exceed the $K_M$ of the enzyme.

Figure 10:
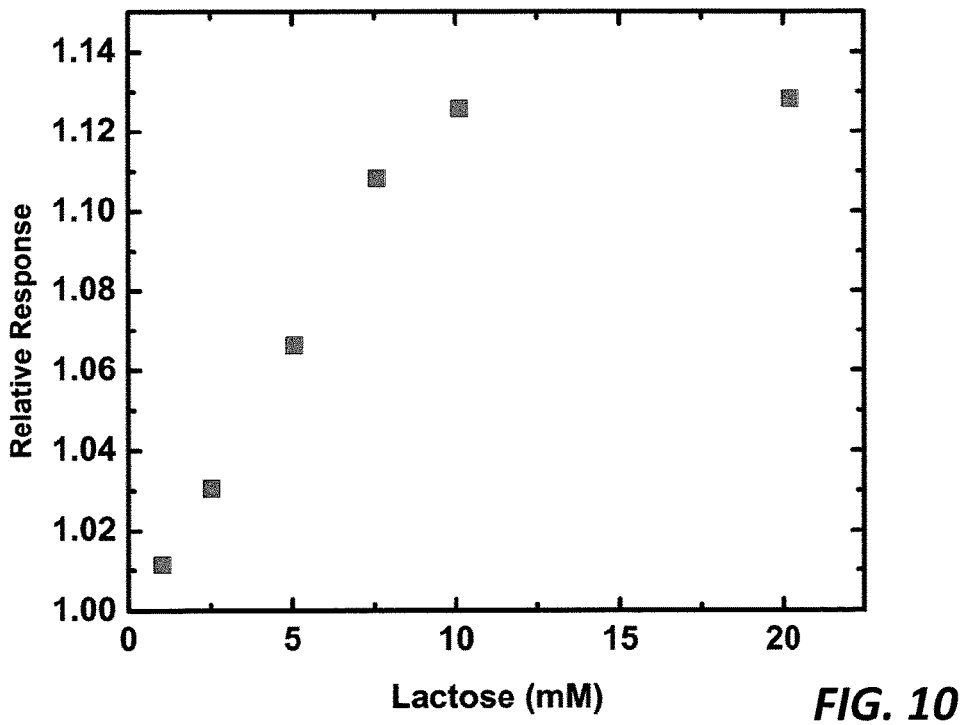
FIG. 10. Response curve for biosensing system B. Biosensing system B is a lactose sensor with a porous diffusive barrier. Signal change was measured relative to a blank solution of phosphate buffered saline (pH 7.4).

Biosensing element B has the addition of a diffusive barrier on top of the enzyme biocomponent layer. This diffusive barrier extended the linear range of biosensing system B into higher concentration ranges, see FIG. 10. For biosensing element B, a porous polycarbonate membrane was immobilized on top of the enzyme biocomponent layer to act as barrier to analyte mass transfer, which resulted in a lower analyte concentration in the enzyme biocomponent layer compared to that in bulk solution.

Figure 11:
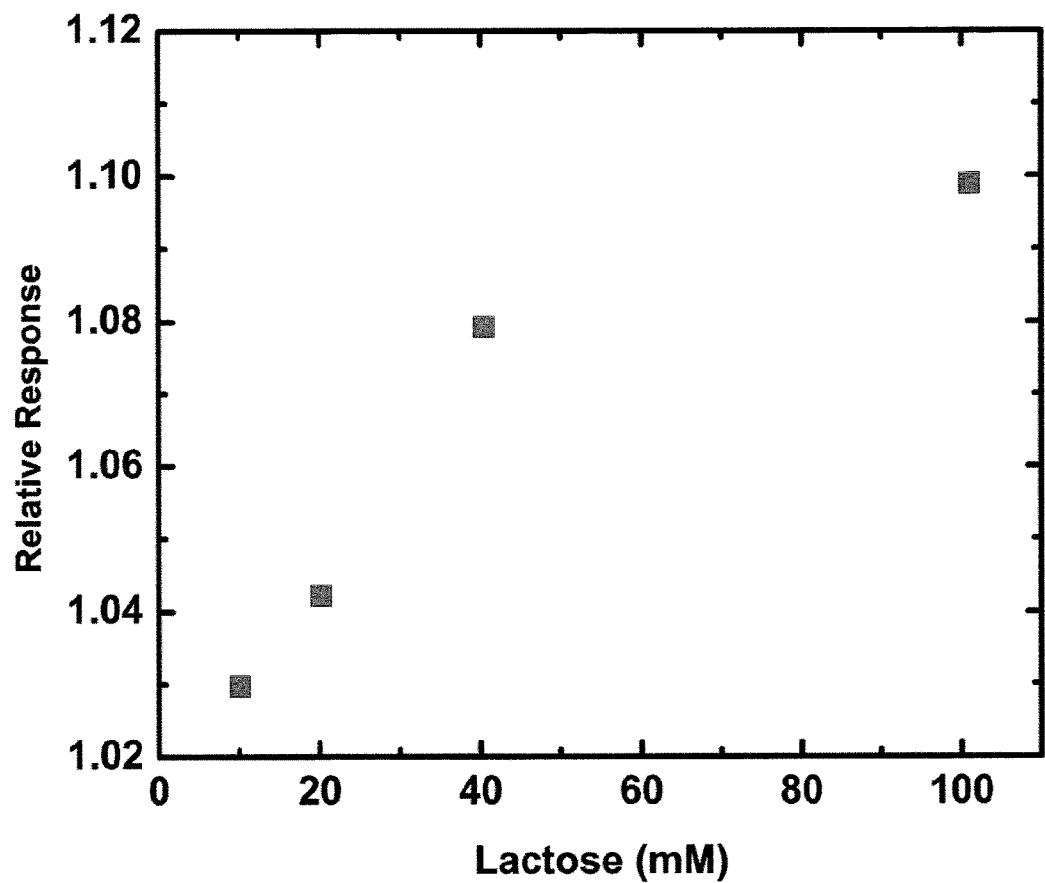
FIG. 11. Response curve for biosensing system C. Biosensing system C is a lactose sensor having a less porous diffusive barrier compared to the porous diffusive barrier used in biosensing system B, see FIG. 10. Signal change was measured relative to a blank solution of phosphate buffered saline (pH 7.4).

Biosensing element C used a less porous polycarbonate membrane relative to the membrane of biosensing element B. This decrease in the porosity of the diffusive barrier resulted in the ability to measure lactose at even higher concentrations relative to biosensing system B, see FIG. 11. The linear response range of biosensing element C was extended into this higher concentration regime as a direct result of the increased mass transfer resistance of the less porous diffusive barrier.

Figure 12:
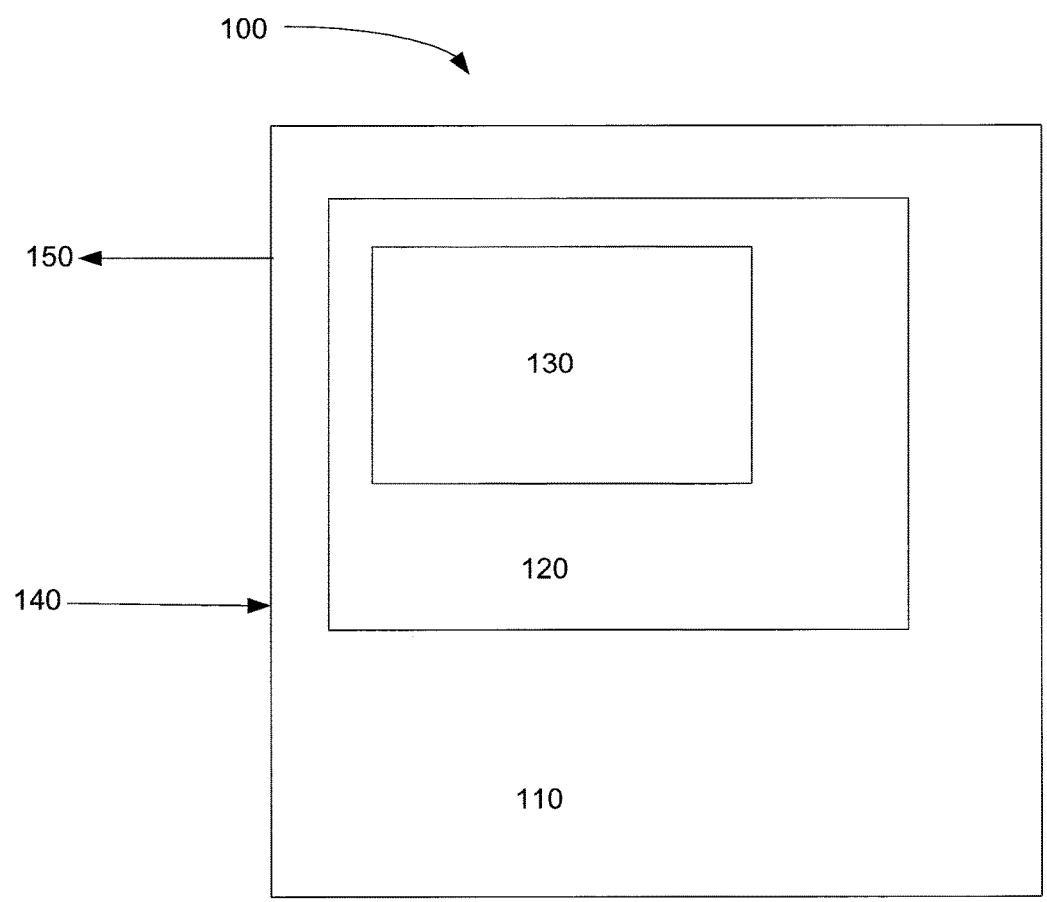
FIG. 12. System for providing design parameters used for constructing biosensing elements.

FIG. 12 shows one exemplary embodiment of a system 100 that is used to provide the appropriate design parameters for constructing biosensing elements used in biosensing systems that have a linear response in a given range of an analyte concentration in a solution. System 100 uses a computer 110 that has a microprocessor 120 that contains software 130 that processes input data 140 to provide output data 150 that contains the appropriate design parameters used for constructing biosensing elements used in biosensing systems that have a linear response in a given range of an analyte concentration in a solution. Output data 150 is displayed upon a screen or saved in a memory storage device or may be transmitted to another memory device or display device.

Effects of Environmental Conditions

Effects of two different environmental conditions on the response characteristics of peroxide and lactose biosensing systems are summarized below.

Figure 3:
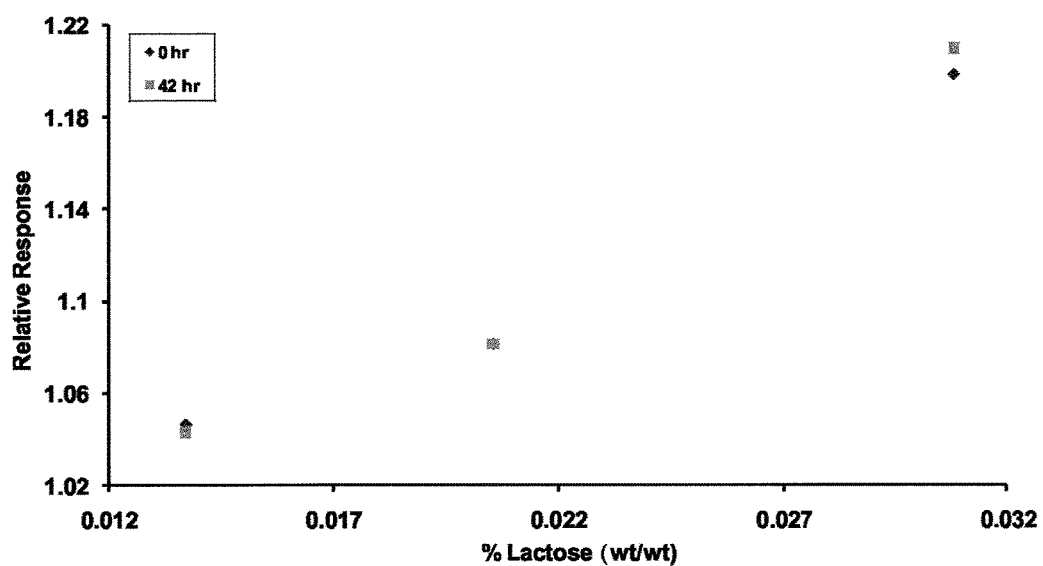
FIG. 3. Response curve generated from lactose standards measured using a lactose biosensing system after 0 and 48 hours in solution at pH 4.8 and 40° C. Signal change was measured relative to a blank solution containing no lactose.
Figure 4:
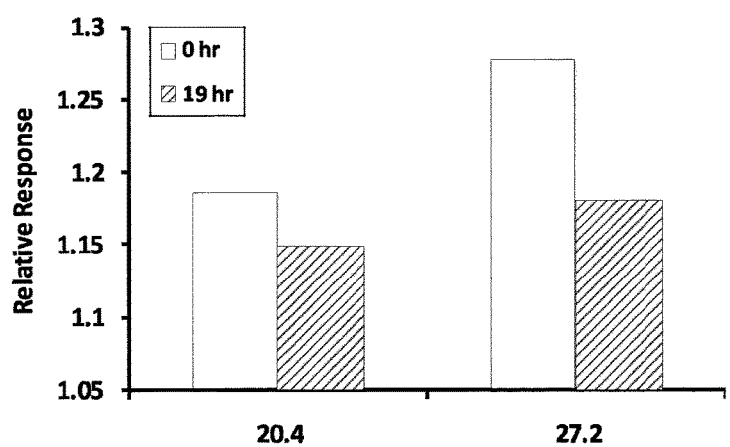
FIG. 4. Response curve generated from $H_2O_2$ standards measured using a peroxide biosensing system after 0 and 19 hours in solution at pH 4.8 and 40° C. Signal change was measured relative to a blank solution containing no $H_2O_2$.

Condition 1. The first set of environmental tests involved exposing biosensing elements to a solution at pH 4.8 and 40° C. for 42 hours. The response of a lactose biosensing system at 0 and 42 h under these conditions is shown in FIG. 3. The enzyme does not lose activity under this set of conditions. Results for the same test with a $H_2O_2$ biosensing system are shown in FIG. 4. The enzyme in this biosensing element lost activity under this given set of environmental conditions.

In a prophetic example, an alternative to making biosensing elements that do not appreciably lose activity during a given amount of time at a given temperature, such as the parameters of condition 1, is to calibrate the biosensing system to account for loss of signal with time.

Figure 5:
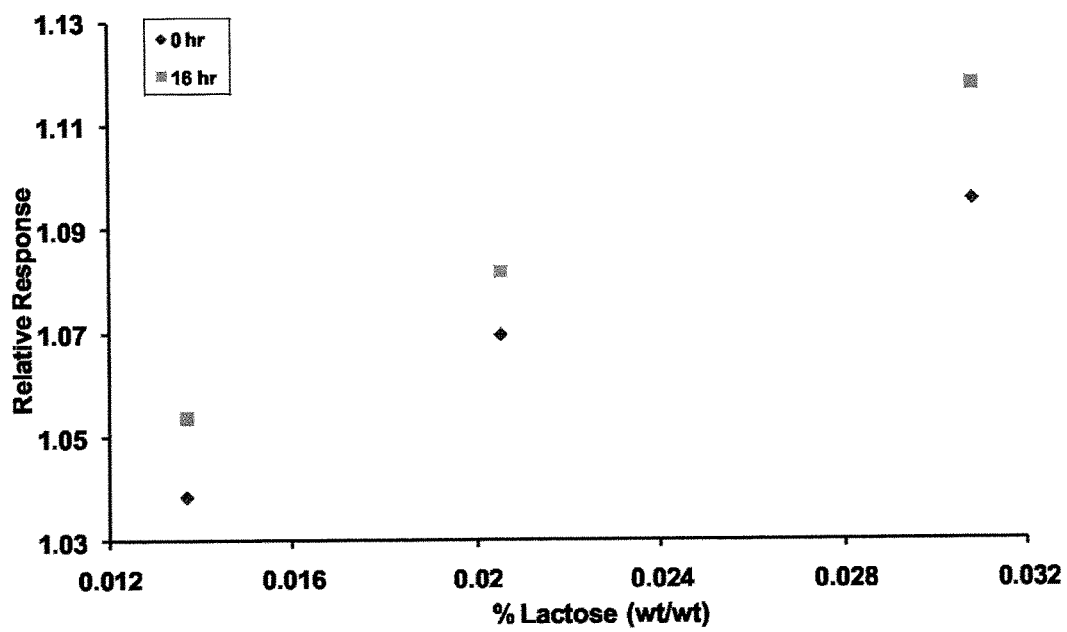
FIG. 5. Response curve generated from lactose standards measured using a lactose biosensing system after 0 and 16 h in solution at pH 6.5 and temperature 49° C. Signal change was measured relative to a blank solution containing no lactose.
Figure 6:
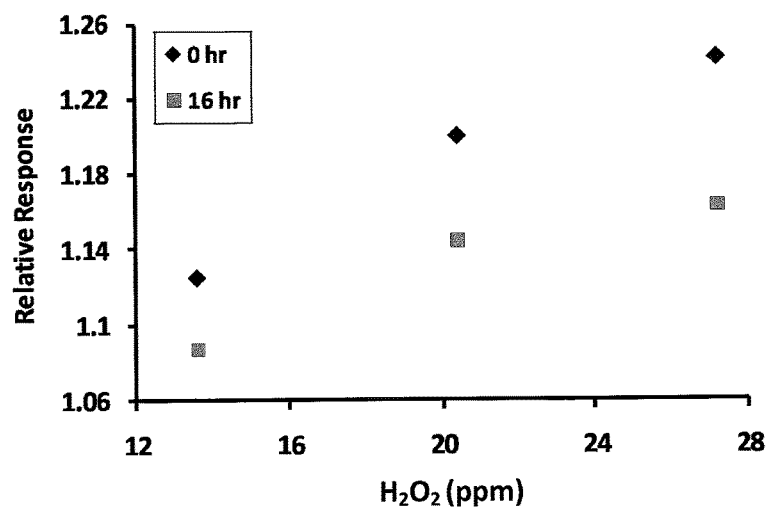
FIG. 6. Response curve generated from $H_2O_2$ standards measured using a peroxide biosensing system after 0 and 16 h in solution at pH 6.5 and temperature 49° C. Signal change was measured relative to a blank solution containing no $H_2O_2$.

Condition 2. The second set of environmental tests involved incubating biosensing elements in a solution at pH 6.5 and 49° C. for 16 hours. Results for the lactose biosensing system are shown in FIG. 5. The stability of this biosensing element was tested over a period of 16 h. The enzyme biocomponent used in this biosensing element was stable under the given set of conditions. FIG. 6 shows a similar experiment conducted with a $H_2O_2$ biosensing element and, like the earlier results seen for Condition 1 using this biosensing element type, there is a decrease in enzyme biocomponent activity over time.

In a prophetic example, an alternative to making biosensing elements that do not appreciably lose activity during a given amount of time at a given temperature, such as the parameters of condition 2, is to calibrate the biosensing system to account for loss of signal with time.

Constructing the Biosensing System and/or Biosensing Element

In an embodiment, the biosensing element is constructed by putting an immobilized biocomponent within a matrix and coupling that biocomponent-containing matrix onto a transducer. In another embodiment, a biosensing system is created by bonding, affixing or otherwise causing the biocomponent to be in contact with an optode.

Figure 13:
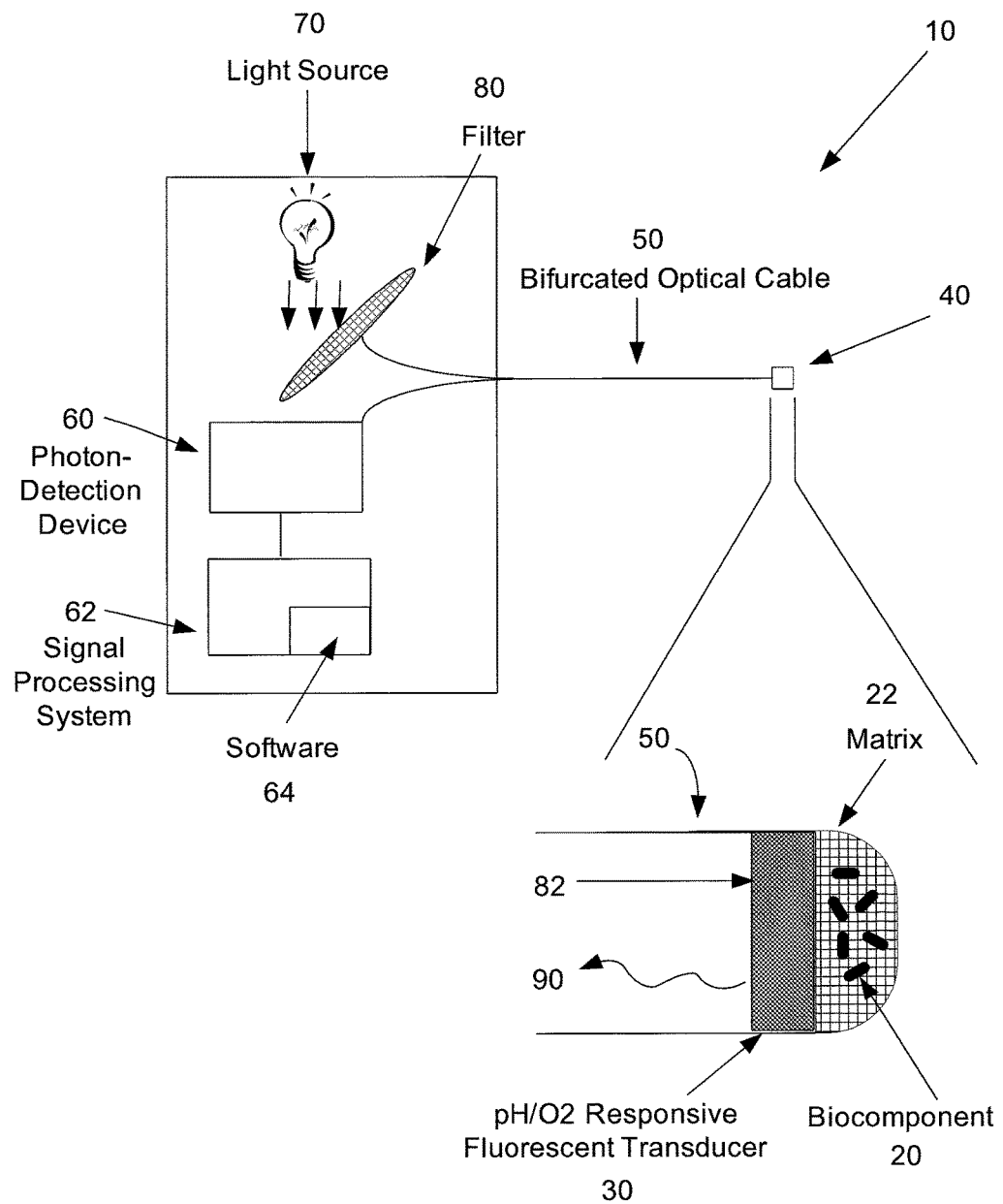
FIG. 13. Schematic representation of a biosensing system.

An embodiment of biosensing system of the present disclosure is depicted in FIG. 13. FIG. 13 depicts a biosensing system 10. Biosensing system 10 includes a biocomponent 20 that is displaced within a matrix 22. Matrix 22 is in direct contact with a transducer 30. Transducer 30 is in direct contact with an end of a bifurcated optical cable 50. Biocomponent 20 and transducer 30 comprise a biosensing element 40. Bifurcated optical cable 50 transmits light from a light source 70 through a filter 80. The light that is transmitted through filter 80 is transmitted through bifurcated optical cable 50 at a first light wavelength 82. Transducer 30 interacts with first light wavelength 82 and luminesces at a second light wavelength 90. Second light wavelength 90 is transmitted through bifurcated optical cable 50 and is detected by a photon-detection device 60 that produces a signal that is sent to a signal processing system 62. Signal processing system 62 contains software 64 that uses an algorithm for determining the concentration of an analyte in a solution based on the luminescence of transducer 30 at second wavelength 90.

Method of Using the Biosensing System and/or Biosensing Element

Figure 14:
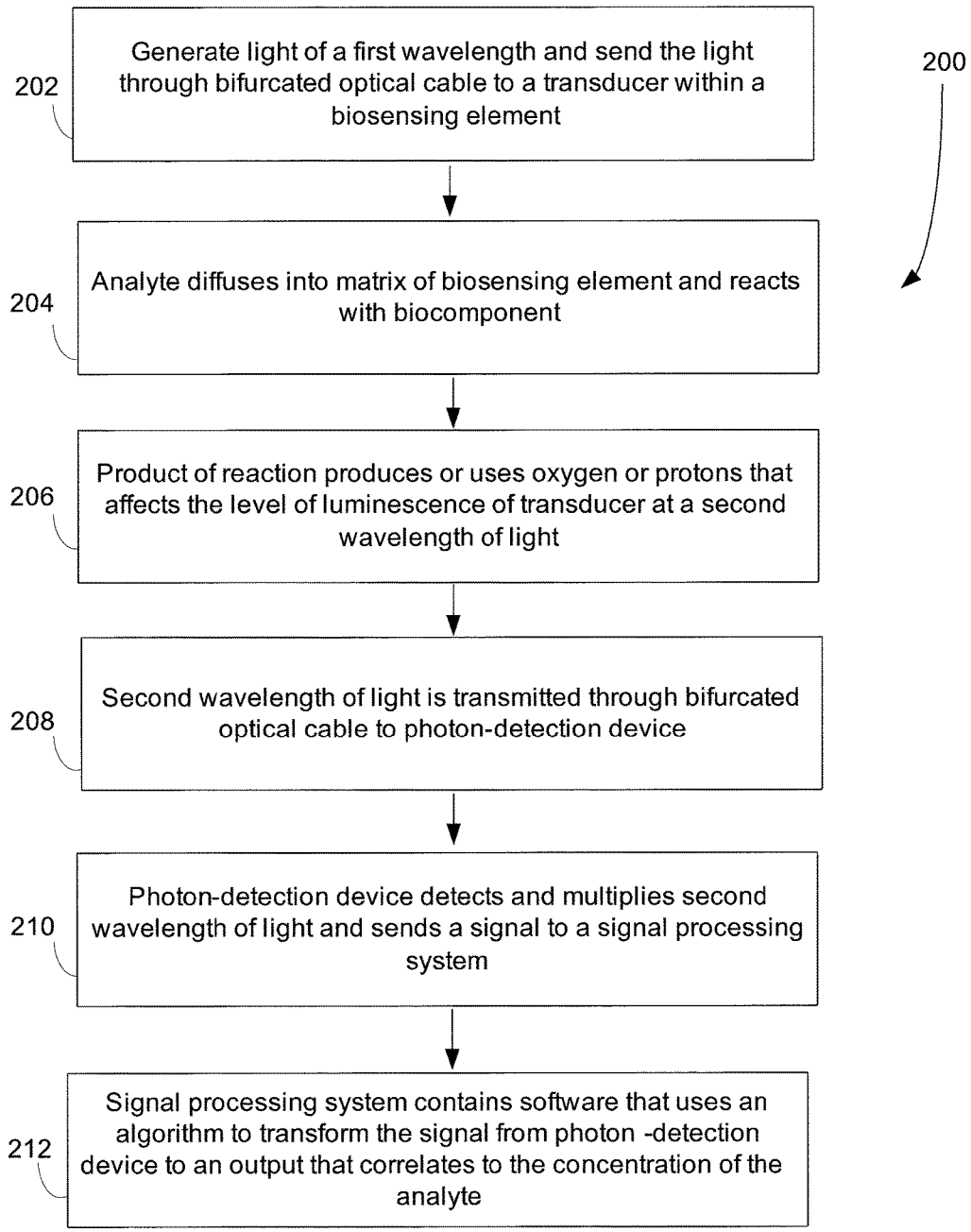
FIG. 14. Schematic representation of exemplary method for using a biosensing system to measure the concentration of an analyte in a solution.

FIG. 14 shows one exemplary method 200 for using a biosensing system to measure the concentration of an analyte in a solution. In step 202, method 200 is implemented by generating light of a first wavelength 82 by light source 70 as it passes through filter 80 and travels down bifurcated optical cable 50 to interact with transducer 30 of biosensing element 40. In step 204, an analyte diffuses into matrix 22 and reacts with biocomponent 20. In step 206, the product of the reaction of the analyte with biocomponent 20 produces or uses oxygen and/or hydrogen ions that interact with transducer 30 to affect the amount of fluorescence at a second light wavelength 90 of transducer 30. In step 208, the second light wavelength 90 is transmitted through bifurcated optical cable 50 and detected by photon-detection device 60. In step 210, photon-detection device 60 detects and multiplies the signal of second light wavelength 90 and sends a signal to signal processing system 62. In step 212, signal processing system 62 has software 64 that uses an algorithm that transforms the signal from photon-detection device 60 into an output that can be read as a numerical representation of the concentration of the analyte.

Immobilization of the Biocomponent

In order to make a biosensing system and/or biosensing element, the biocomponent needs to be sufficiently bound to or in contact with the transducer. This can be achieved by immobilizing the biocomponent on the transducer. The viability of a biosensing system and/or biosensing element depends on the processing and type of material used for immobilizing the biocomponent. The material used for immobilizing the biocomponent may be referred to as a matrix, matrix material or as an immobilizing material.

Biocomponents may be very sensitive to the immobilizing process and the material that is used for immobilization. The immobilization process should not damage the biocomponent. The pH, ionic-strength, and any other latent chemistries of the matrix should be compatible with the biocomponent. The reactants and products of the biocomponent should not affect the material used for immobilization. The biocomponent should be effectively immobilized and there should not be any leakage of the biocomponent from the matrix during the active lifetime of the biosensing system and/or biosensing element. The immobilization material should be non-toxic and non-polluting. The material should have proper permeability to allow sufficient diffusion of substrates, products and gases. The matrix material should allow for sufficient cell activity and cell density. The immobilization material should protect the biocomponent from biotic and abiotic environmental stresses that would lower biocomponent activity or lifetime.

Techniques of Immobilization

In one embodiment, adsorption is used to immobilize the biocomponent. Many substances adsorb enzymes, cells, microorganisms and other biocomponents on their surfaces, e.g., alumina, charcoal, clay, cellulose, kaolin, silica gel and collagen. Adsorption can be classified as physical adsorption (physisorption) and chemical adsorption (chemisorption). Physisorption is usually weak and occurs via the formation of van der Waals bonds or hydrogen bonds between the substrate and the enzyme molecules. Chemisorption is much stronger and involves the formation of covalent bonds. Adsorption of the biocomponent may be specific through the interaction of some moiety, link or other reactive component of the biocomponent or may be non-specific.

In another embodiment, microencapsulation is used to immobilize the biocomponent. In this method, a thin microporous semipermeable membrane is used to surround the biocomponent. Because of the proximity between the biocomponent and the transducer and the very small thickness of the membrane, the biosensing element response is fast and accurate. In one embodiment the biocomponent is bonded to the sensor via molecules that conduct electrons, such as polypyrrole. The membrane used for microencapsulation may also serve additional functions such as selective ion permeability, enhanced electrochemical conductivity or mediation of electron transfer processes. Examples of membranes that may be used for microencapsulation immobilization of biocomponents are cellulose acetate, polycarbonate, collage, acrylate copolymers, poly(ethylene glycol) and polytetrafluoroethylene (PTFE). Additional materials that may be used are agarose, and alginate and polylysine, which together form an alginate-polylysine-alginate microcapsule.

In another embodiment, entrapment is used to immobilize the biocomponent. In this method cells are physically constrained (entrapped) to stay inside a three-dimensional matrix. The materials used for entrapment must allow uniform cell distribution, biocompatibility and good transport of substrates and products. Both natural and synthetic materials (like alginate, agarose and collagen) may be used for entrapment.

In another embodiment, hydrogels are used to immobilize the biocomponent. Hydrogels provide a hydrophilic environment for the biocomponent and they require only mild conditions to polymerize. Hydrogels are capable of absorbing large quantities of water which can facilitate reactions such as hydrolysis. Both natural and synthetic hydrogels may be used such as algal polysaccharides, agar, agarose, alginate, and carrageenan, polyacrylamide, polystyrene and polyurethane.

Alginate, a hydrogel, provides a good, biocompatible microenvironment for the biocomponent with gentle encapsulation process. It is a naturally occurring linear polymer composed of ß-(1,4)-linked D-mannuronic acid and a-(1,4)-L-guluronic acid monomers. Commercially, alginate is obtained from kelp, but bacteria such as *Azotobacter vinelandii*, several *Pseudomonas* species and various algae also produce it. When alginate is exposed to $Ca^{2+}$ ions, a cross-linking network is formed by the bonding of $Ca^{2+}$ ions and polyguluronic portions of the polymer strand by a process known as ionic gelation. The gelation process is temperature-independent. Complete gelling time without biocomponents may be from about 1 minute to greater than about 30 minutes. Gelling time usually increases with an increase in biocomponent density and decreases with an increase in $CaCl_2$ concentration.

In another embodiment, sol-gels may be used to entrap biocomponents into silicate networks. Sol-gels may require milder polymerization processes and create matrices that exhibit good mass transport and molecular access properties particularly for electrochemical and optical transduction modes.

In another embodiment, cross-linking is used to immobilize the biocomponent. Cross-linking chemically bonds the biocomponent to solid supports or to other supporting materials such as a gel. Bifunctional agents such as glutaraldehyde, hexamethylene diisocyanate and 1,5-dinitro-2,4-difluorobenzene may be used to bind the biocomponent to the solid support. Cross-linking produces long-term stability under more strenuous experimental conditions, such as exposure to flowing samples, stirring, washing, etc.

In another embodiment, covalent bonding is used to immobilize the biocomponent. Covalent bonding uses a particular group present in the biocomponent, which is not involved in catalytic action, and attaches it to the support matrix (transducer or membrane) through a covalent bond. The radicals that take part in this reaction are generally nucleophilic in nature (e.g., —$NH_2$, —COOH, —OH, —SH and imidazole groups).

Stabilization

Biosensing systems and biosensing elements of the present disclosure are stable and long-lived, can stand prolonged storage and can also perform well in use for extended periods. Biocomponents may be stabilized through various means, depending upon the type of biocomponent and transducer used.

In one embodiment, the biocomponent may be stabilized through molecular modification. Molecular modification improves the stability of enzymes, and other biocomponents, through changing certain amino acids or nucleotides in the peptide or nucleic acid sequence, respectively. Molecular modifications may increase the temperature stability of various enzymes by modifying the amino acids at the catalytically active enzyme reaction site, through site-directed mutagenesis.

Another method for improving the stability of biocomponents, such as enzymes, is through glycosylation. Since glycosylated proteins are very stable, grafting or otherwise bonding polysaccharides or short chains of sugar molecules onto protein molecules usually improves the stability of the biocomponent.

In one embodiment, the biocomponent may be stabilized through cross-linking. Cross-linking of the biocomponent may occur through covalent bonding, entrapment, encapsulation and other immobilization techniques or processes. These immobilization processes can improve enzyme stability by reducing the biocomponent's mobility and thereby reducing degradation of its three-dimensional structure. In addition, cross-linking prevents the loss of biocomponents from their immobilized matrix. Using the entrapment method discussed above, the loss of biocomponents may further be reduced by the addition of certain gel-hardening agents such as glutaraldehyde, polyethyleneimine, hexamethylenediamine and formaldehyde.

In another embodiment for stabilizing the biocomponent, freeze drying, also known as lyophilization, may be used. Freeze drying is a method for long-term preservation of microorganisms and enzymes. It involves removal of water from frozen bacterial suspensions by sublimation under reduced pressure. The lyophilization is performed in the presence of cryoprotective agents such as glycerol and DMSO which reduce the damage caused during freezing and during thawing. Lyophilized biocomponents, for example dried cells, are stable to degradation by keeping the lyophilized biocomponents below 4° C., and away from oxygen, moisture and light. Even after prolonged periods of storage, such as about 10 years, lyophilized biocomponents may then be rehydrated and restored to an active state. Two examples of lyophilizing of biocomponents include centrifugal freeze-drying and prefreezing.

In another embodiment, the biocomponents may be stabilized through heat shocking. Heat shocking involves heating vacuum-dried cells at a high temperature (about 300° C. for example) for a very short time (about 2-3 minutes for example). With the proper combination of temperature and heating time, biocomponents such as whole cells and microorganisms can be killed but still retain an active enzyme system that may be used to detect a compound of interest. These dead cells and microorganisms can be kept for a long time away from moisture without any requirement of nutrients.

In another embodiment, the addition of carbohydrates and other polymers will stabilize the biocomponents. Carbohydrates used to stabilize biocomponents include polyalcohols and various sugars such as trehalose, maltose, lactose, sucrose, glucose and galactose, for example. This stabilization may occur due to the interaction of polyhydroxyl moieties from the polyalcohols and/or sugars with water with the biocomponents, thus increasing hydrophobic interactions and keeping the biocomponents in a stable conformation.

In an additional embodiment, stabilization of the biocomponents may occur through freezing the biocomponents. When a biocomponent is frozen, the metabolic activities may be reduced considerably. Storage of the biosensing elements at temperatures wherein the biocomponents remain frozen may increase the stability and lifetime of the biosensing system.

EXAMPLES pH Optode Construction

Plastic clad fiber optic cables with core diameter of 1 mm and length of 6-8 inches were used to make biosensing elements for use in biosensing systems. The first 1.5 to 3 mm of cladding was removed from both ends of these cables using wire strippers, taking care not to scratch the sides of the fiber. Each surface was now polished in a FIG. 8 pattern using polishing glass, fine grit papers and a polishing disc which held the optical fiber perpendicular to the polishing surface. After polishing, each end was cleaned with isopropyl alcohol and examined at 100× magnification under a microscope to ensure that there were no scratches through the core and no chips in the edges that extend into the core of the fiber. The smooth surface of the fiber-end was necessary in order to have a stable response and to reduce signal losses due to refraction of light. Around 5 mm of cladding was removed again from one of the ends of the fiber in order to insert a connector ferrule which connects each sensor to the 1 m long optical fiber. From the sensing end around 1 mm of the cladding was removed. Each of these cables was fit with a gasket and a cap to fit a 2 mL glass vial at the sensing end.

The pH optode was formed using a modified immobilization procedure by affixing a pH-sensitive fluorescent dye to the end of the fiber optic cable. At first, 0.5 g of cyanuric chloride was dissolved in 20 mL of acetone. To this solution, 1.0 g of polyvinyl alcohol (PVA, MW=10,000) and 10 mL of deionized water ($dH_2O$) were added. After mixing for 17 minutes at room temperature, this solution was filtered and the resultant filtrate was washed with a mixture of water/acetone (1:2). This filtrate was then added in a solution containing 100 mg of fluoresceinamine in 10 mL acetone. The mixture was allowed to react for 35 minutes, then was filtered, washed with small amount of acetone (~10 mL) and subsequently dried.

In order to make the hydrogel, 5 µL of 6M HCl (acts as catalyst), 5 µL of 5% (v/v) solution of glutaraldehyde (Grade 1: 50% solution) and 25 µL of 5% (w/v) of PVA/fluoresceinamine dye in $dH_2O$ were mixed together. One drop of this mixture was added to the tip of the optical fiber using a 100 µL pipette and allowed to polymerize for ~30 seconds. Prior to the transfer step, the fiber optic end was cleaned by exposure to 2 M HCl followed by washing with water and then drying. This was important as the hydrogel adhered best to a cleaned surface. After the tip was coated, it was then stored in 0.1 M $Na_2HPO_4$ (Sigma Chemicals, 99% purity) at room temperature.

In order to test the performance of each pH optode, these probes were connected to the detector system and the pH optode was allowed to reach equilibrium (>99% of steady state value) in a phosphate buffer solution at a pH of 7. Once it reached equilibrium (allowed to stay at equilibrium for couple of minutes), it was then transferred to another solution phosphate buffer having a pH of 6.9 and allowed to reach a new equilibrium (response time of about 3 to about 5 minutes). These values of pH of the buffer solution were chosen because they lie in the groundwater pH range in which biosensing element would be finally tested. These readings were taken at 800 V and the PMT amplifier adjusted to obtain a signal in the linear response range. Two criteria used in deciding whether the biosensing element is good enough or not were the magnitude of the change in equilibrium value (more is better) and stability in the biosensing element response.

Preparation of Biocomponent

Cell Cultures

Cells may be grown and isolated by methods well known in the art. In order to make a biosensing system, cells were immobilized using the entrapment method. The cells used for immobilization had been stored at 4° C. in a phosphate-buffered saline solution. This cell suspension was centrifuged at 15000×g for 2 minutes. The cell pellet was then washed with saline (9 g/L of NaOH [pH 7.1]) and again centrifuged. This cycle was repeated three times. Then a 4% (w/v) aqueous solution of Na-alginate was added at a ratio of about 1.0 to about 1.2 g/g. Next, the sides of the pH optode were carefully rinsed and wiped to remove any traces of phosphate, which inhibits gelation. The cell-alginate mixture was stirred well with a pipette tip and a small drop of gel was carefully deposited on the tip of the pH optode. The tip was now dipped into an ice-cold solution of 7% (w/v) of $CaCl_2 \cdot 2H_2O$ for 15 minutes. When exposed to $Ca^{2+}$ ions, a cross-linking network was formed by the bonding of $Ca^{2+}$ ions and polyguluronic portions of the polymer strand by a process known as ionic gelation. Gelling time increases with increase in cell density and decreases with increase in $CaCl_2$ concentration. After immobilization, the diameter of the biosensing element on the tip was about 2 mm. Once the biosensing element was made, it was stored in the measurement solution (NaOH solution [pH 7.0] in which all the readings were taken).

Although the pH-sensitive dye layer is quite stable physically and does not easily fall off from the optode tip, it is advisable not to touch the optode surface with a pipette tip. Also, in order to have a stable response, it was important that no bubbles were present inside the bead after immobilization.

Preparation of Biosensing Element Using Dry-Heated Cells

In order to prepare dry heated cells, cells stored at 4° C. in phosphate-buffered saline solution were centrifuged at 15,000×g for 3 minutes and were washed twice with distilled water. These cells were suspended in a small quantity of water (3 mL of stored cell suspension were washed and then suspended in 0.5 mL of water). This suspension was put in a 10-mL beaker and water was completely removed by vacuum drying at 35° C. It took about an hour to dry these cells. The dried cells were then scratched off from the surface of beaker using a spatula. The beaker was then covered with aluminum foil and left in the oven at a constant temperature of 270° C. and for a given period of time (30 sec, 60 sec, etc.). These dry heated cells looked like a highly porous solid and had a light orange color. These dry-heated cells (~0.003-0.004 g) were also immobilized using the same entrapment method. However it was found that when these cells were directly mixed with 4% (w/v) of alginate, there were a lot of small bubbles in the cell-alginate mixture. Since it was important to eliminate these bubbles in order to obtain a stable response, these cells were first suspended in 10 μL of NaOH (pH 7.0) in a 1.5 mL-vial and then 8% (w/v) of alginate was added to it (from about 0.3 to about 0.5 μg of dry wt. of cells to wt. of alginate). This mixture was used to make the biosensing element.

Preparation of Biosensing Element Using Chloramphenicol-Treated Cells

Cells stored at 4° C. in phosphate-buffered saline were centrifuged at 15,000×g for 2 minutes and the pellet was then washed twice with saline (9 g/L of NaCl [pH 7.1]) containing 50 μg/mL of chloramphenicol. Next, sodium alginate (4% w/v in water) containing either 50 or 200 μg/mL of chloramphenicol was added and mixed well with the cell pellet. This cell and alginate mixture was kept for 5 minutes at room temperature before it was used to make the biosensing element.

Preparation of Biosensing Element Using Protease Inhibitor-Treated Cells

Cells stored at 4° C. in phosphate-buffered saline were centrifuged at 15,000×g for 2 minutes and the pellet was then washed twice with saline (9 g/L of NaCl [pH 7.1]) containing 5 μL of protease inhibitor cocktail in 1 mL of saline solution. This cocktail was prepared by adding 215 mg of lyophilized protease inhibitor in a solution containing 1 mL of DMSO (Dimethyl sulfoxide) and 4 mL of deionized water. The cocktail had a broad specificity for the inhibition of serine, cysteine, aspartic and metalloproteases, and aminopeptidases. It was stored at −20° C. in the freezer. These cells were then mixed with Na-alginate solution (4% w/v) containing 200 μL of cocktail per mL of alginate solution. The cell-alginate mixture was left for about 5 minutes at room temperature before it was used for making the biosensing element. The ratio of the weight of wet cells to the weight of alginate used in the experiment was 0.72 g/g.

Preparation of Biosensing Element with a Poly-L-Lysine Coating

The alginate bead was coated with poly-L-lysine (PLL) by preparing the tip of a biosensing element with a biocomponent as described above. The Ca-alginate bead on the biosensing element tip was then washed twice with saline solution (9 g/L of NaCl in water). Then the tip of the biosensing element was immersed in 10 mL of 0.4% (w/v) of poly-L-lysine.HCl solution, stored at 4° C. inside the refrigerator) in saline for 30 minutes at 30° C.

Oxygen Optode Construction

In one embodiment, the transducer used in a biosensing system is an oxygen optode. An oxygen optode is a sensor based on optical measurement of the oxygen concentration. In one embodiment, a chemical film is glued to the tip of an optical cable and the fluorescence properties of this film depend on the oxygen concentration. Fluorescence is at a maximum when there is no oxygen present. When an $O_2$ molecule collides with the film, it quenches the photoluminescence. In a given oxygen concentration, there will be a specific number of $O_2$ molecules colliding with the film at any given time, and the fluorescence properties will be stable.

In one example, a biosensing system for measuring the concentration of oxygen consisted of a layer of immobilized whole cells over an oxygen optode, which was constructed from a 25-cm section of PMMA optical fiber terminated with a straight tip connector. The fiber jacket was detached 1 mm from the end (non-connector terminated) and then polished with 2000-grit and 3 μm polishing film (part of a fiber optic tool kit, IF-TK4-RP2, Industrial Fiber Optics) to minimize potential signal loss due to scattering. One mg of the oxygen-sensitive phosphorophore RuDPP, which is classified as a phosphorophore since its decay lifetime is longer than typical fluorophores, was dissolved into 1 mL chloroform and mixed with 200 mg silicone gel (clear RTV silicone, Permatex, Inc.). A 1-μL aliquot of this mixture was then added to the polished fiber tip. The RuDPP gel layer was affixed to the optical fiber end as soon as the chloroform evaporated. In one prophetic example, previously stored *E. coli* whole cells (with different plasmids which may encode for galactosidases, lactose oxidases, carbohydrate oxidases, glucose oxidases, galactose oxidases, cellobiose dehydrogenases, and/or catalases, for example) were centrifuged and mixed with sodium alginate solution (2.5%) in a cell-to-alginate ratio (wet cell mass:alginate solution) of 1:1 w/w unless otherwise specified. In one example, purified enzymes comprising galactosidases, lactose oxidases, carbohydrate oxidases, glucose oxidases, galactose oxidases, cellobiose dehydrogenases, and/or catalases, for example, were mixed with sodium alginate solution (2.5%) in a cell-to-alginate ratio (wet cell mass:alginate solution) of 1:1 w/w unless otherwise specified. Two 1 µL of the cell-alginate mixture was placed on the tip of each oxygen optode and immobilized after immersing the optode in 0.47 M calcium chloride solution for 30 min at 0° C. All biosensing elements were stored at 0° C. in a measurement solution of 0.15 M NaCl and 0.025 M $CaCl_2$ at pH 7.0.

Oxygen Optode Based Biosensing System

In one example, the oxygen optode based biosensing system instrumentation consisted of two separate optoelectronic modules: a 470-nm LED and a 450/60 nm optical bandpass filter (Chroma Technologies) as the excitation light source, and a computer-controlled Ocean Optics USB4000-FL spectrometer with 10 nm resolution for detection. The 470-nm excitation light was delivered through one leg of a bifurcated optical fiber assembly that has two 1-mm fibers side-by-side in the common end (Ocean Optics, Inc.), which was connected with the biosensing system via a straight tip connector. The phosphorescent emission light (peak at 620 nm) from the biosensing system was directed back into the detector through the other leg of the bifurcated optical fiber and measured by the spectrometer (sensitivity of approximately 60 photons/count at 600 nm). The spectrometer output from 615 nm to 625 nm was integrated over 200 ms and five such values were averaged to yield one measurement value per second. The change in the intensity or change in the lifetime decay of the emission light over time correlates to the oxygen concentration change at the RuDPP layer of the biosensing element.

The above examples, embodiments, definitions and explanations should not be taken as limiting the full metes and bounds of the invention.

REFERENCES

The contents of the following references are hereby incorporated into the present disclosure:

Ikeda et al., J. Electroanal. Chem. 361 (1993) 221.

Safina et al., Electrochimica Acta 55 (2010) 7690-7695.

Roda A, Cevenini L, Michelini E, Branchini B R. A portable bioluminescence engineered cell-based biosensor for on-site applications. Biosens Bioelectron. 2011 Apr. 15; 26(8):3647-53. Epub 2011 Feb. 18.

Sezgintürk M K, Dinçkaya E. A Biosensor for the Determination of β-galactosidase Activity: A Different Viewpoint on Biosensors. Artif Cells Blood Substit Immobil Biotechnol. 2011 Feb. 25.

Sezgintürk M K, Dinçkaya E. β-galactosidase Determination by an Electrochemical Biosensor Mediated with Ferrocene. Artif Cells Blood Substit Immobil Biotechnol. 2011 Feb. 22.

Leal M P, Assali M, Fernandez I, Khiar N. Copper-catalyzed azide-alkyne cycloaddition in the synthesis of polydiacetylene: "click glycoliposome" as biosensors for the specific detection of lectins. Chemistry. 2011 Feb. 7; 17(6):1828-36.

Veetil J V, Jin S, Ye K. A glucose sensor protein for continuous glucose monitoring. Biosens Bioelectron. 2010 Dec. 15; 26(4):1650-5.

Moreira F T, Kamel A H, Guerreiro J R, Sales M G. Man-tailored biomimetic sensor of molecularly imprinted materials for the potentiometric measurement of oxytetracycline. Biosens Bioelectron. 2010 Oct. 15; 26(2):566-74.

Yang C, Zhang Z, Shi Z, Xue P, Chang P, Yan R. Application of a novel co-enzyme reactor in chemiluminescence flow-through biosensor for determination of lactose. Talanta. 2010 Jun. 30; 82(1):319-24.

Ren X, Yang L, Tang F, Yan C, Ren J. Enzyme biosensor based on NAD-sensitive quantum dots. Biosens Bioelectron. 2010 Sep. 15; 26(1):271-4.

Conzuelo F, Gamella M, Campuzano S, Ruiz M A, Reviejo A J, Pingarrón J M. An integrated amperometric biosensor for the determination of lactose in milk and dairy products. J Agric Food Chem. 2010 Jun. 23; 58(12):7141-8.

Nagatsuka T, Uzawa H, Ohsawa I, Seto Y, Nishida Y. Use of lactose against the deadly biological toxin ricin. ACS Appl Mater Interfaces. 2010 April; 2(4):1081-5.

Kawsar S M, Matsumoto R, Fujii Y, Yasumitsu H, Dogasaki C, Hosono M, Nitta K, Hamako J, Matsui T, Kojima N, Ozeki Y. Purification and biochemical characterization of a D-galactose binding lectin from Japanese sea hare (Aplysia kurodai) eggs. Biochemistry (Mosc). 2009 July; 74(7):709-16.

Munoz F J, Pérez J, Rumbero A, Santos J I, Canada F J, André S, Gabius H J, Jiménez-Barbero J, Sinisterra J V, Hernáiz M J. Glycan tagging to produce bioactive ligands for a surface plasmon resonance study via immobilization on different surfaces. Bioconjug Chem. 2009 April; 20(4): 673-82.

Jenkins D M, Teruel M A, Reyes-de-Corcuera J I, Young O. Simultaneous determination of hydrolysis and mutarotation rates during the enzymatic hydrolysis of lactose. J Agric Food Chem. 2008 Sep. 24; 56(18):8303-8.

Sezgintürk M K, Dinçkaya E. Beta-galactosidase monitoring by a biosensor based on Clark electrode: its optimization, characterization and application. Biosens Bioelectron. 2008 Jul. 15; 23(12):1799-804.

Varshney M, Li Y. Double interdigitated array microelectrode-based impedance biosensor for detection of viable Escherichia coli O157:H7 in growth medium. Talanta. 2008 Jan. 15; 74(4):518-25.

Mora F, Tran D H, Oudry N, Hopfgartner G, Jeannerat D, Sakai N, Matile S. Interface engineering of synthetic pores: towards hypersensitive biosensors. Chemistry. 2008; 14(6):1947-53.

Seo J H, Adachi K, Lee B K, Kang D G, Kim Y K, Kim K R, Lee H Y, Kawai T, Cha H J. Facile and rapid direct gold surface immobilization with controlled orientation for carbohydrates. Bioconjug Chem. 2007 November-December; 18(6):2197-201.

Sharma S K, Kumar A, Chaudhary R, Suman, Pundir C S, Sehgal N. Lactose biosensor based on lactase and galactose oxidase immobilized in polyvinyl formal. Artif Cells Blood Substit Immobil Biotechnol. 2007; 35(4):421-30.

Betancor L, Luckarift H R, Seo J H, Brand O, Spain J C. Three-dimensional immobilization of beta-galactosidase on a silicon surface. Biotechnol Bioeng. 2008 Feb. 1; 99(2):261-7.

Stoica L, Ruzgas T, Ludwig R, Haltrich D, Gorton L. Direct electron transfer—a favorite electron route for cellobiose dehydrogenase (CDH) from Trametes villosa. Comparison with CDH from Phanerochaete chrysosporium. Langmuir. 2006 Dec. 5; 22(25):10801-6.

Turishcheva GKh, Kazarinov I A, Ignatov O V, Ignatov V V. [A bioelectrochemical study of a suspension of Escherichia coli cells metabolizing glucose and lactose]. Mikrobiologiia. 2006 January-February; 75(1):52-6. Russian.

Zhang Y, Luo S, Tang Y, Yu L, Hou K Y, Cheng J P, Zeng X, Wang P G. Carbohydrate-protein interactions by "clicked" carbohydrate self-assembled monolayers. Anal Chem. 2006 Mar. 15; 78(6):2001-8.

Stoica L, Ludwig R, Haltrich D, Gorton L. Third-generation biosensor for lactose based on newly discovered cellobiose dehydrogenase. Anal Chem. 2006 Jan. 15; 78(2):393-8.

Maestre E, Katakis I, Narváez A, Dominguez E. A multianalyte flow electrochemical cell: application to the simultaneous determination of carbohydrates based on bioelectrocatalytic detection. Biosens Bioelectron. 2005 Nov. 15; 21(5):774-81. PubMed PMID: 16242617.

Sharma S K, Singhal R, Malhotra B D, Sehgal N, Kumar A. Lactose biosensor based on Langmuir-Blodgett films of poly(3-hexyl thiophene). Biosens Bioelectron. 2004 Oct. 15; 20(3):651-7.

Jenkins D M, Delwiche M J. Adaptation of a manometric biosensor to measure glucose and lactose. Biosens Bioelectron. 2003 January; 18(1):101-7.

Rajendran V, Lrudayaraj J. Detection of glucose, galactose, and lactose in milk with a microdialysis-coupled flow injection amperometric sensor. J Dairy Sci. 2002 June; 85(6):1357-61.

Curey T E, Salazar M A, Oliveira P, Javier J, Dennis P J, Rao P, Shear J B. Enzyme-based sensor arrays for rapid characterization of complex disaccharide solutions. Anal Biochem. 2002 Apr. 1; 303(1):42-8.

Lehmann M, Riedel K, Adler K, Kunze G. Amperometric measurement of copper ions with a deputy substrate using a novel *Saccharomyces cerevisiae* sensor. Biosens Bioelectron. 2000 June; 15(3-4):211-9.

Ramakrishnan A, Sadana A. Analyte-receptor binding and dissociation kinetics for biosensor applications: a fractal analysis. Biosens Bioelectron. 2000; 15(11-12):651-62.

Eshkenazi I, Sacks V, Neufeld T, Rishpon J. Amperometric biosensors based on microflow injection system. Appl Biochem Biotechnol. 2000 November-December; 89(2-3):217-30.

Eshkenazi I, Maltz E, Zion B, Rishpon J. A three-cascaded-enzymes biosensor to determine lactose concentration in raw milk. J Dairy Sci. 2000 September; 83(9):1939-45.

Tkác J, Sturdik E, Gemeiner P. Novel glucose non-interference biosensor for lactose detection based on galactose oxidase-peroxidase with and without co-immobilised beta-galactosidase. Analyst. 2000 July; 125(7):1285-9.

Svitel J, Curilla O, Tkác J. Microbial cell-based biosensor for sensing glucose, sucrose or lactose. Biotechnol Appl Biochem. 1998 April; 27 (Pt 2):153-8.

Sorochinskiĭ V V, Kurganov B I. [Biosensors for detecting organic compounds. II. Sensors for carbohydrates, aromatic, heterocyclic and other organic compounds]. Prikl Biokhim Mikrobiol. 1998 January-February; 34(1):22-42. Review. Russian.

Ruzgas T, Csöregi E, Katakis I, Kenausis G, Gorton L. Preliminary investigations of an amperometric oligosaccharide dehydrogenase-based electrode for the detection of glucose and some other low molecular weight saccharides. J Mol Recognit. 1996 September-December; 9(5-6):480-4.

Szabó E E, Adányi N, Váradi M. Application of biosensor for monitoring galactose content. Biosens Bioelectron. 1996; 11(10):1051-8.

Filipiak M, Fludra K, Gościmińska E. Enzymatic membranes for determination of some disaccharides by means of an oxygen electrode. Biosens Bioelectron. 1996; 11(4):355-64.

Sriyudthsak M, Cholapranee T, Sawadsaringkarn M, Yupongchaey N, Jaiwang P. Enzyme-epoxy membrane based glucose analyzing system and medical applications. Biosens Bioelectron. 1996; 11(8):735-42.

Katsu T, Zhang X, Rechnitz G A. Simultaneous determination of lactose and glucose in milk using two working enzyme electrodes. Talanta. 1994 June; 41(6):843-8.

Carlsson H, Ljungcrantz P, Lindbladh C, Persson M, Billow L. Use of genetically prepared enzyme conjugates in lactose and galactose analyses. Anal Biochem. 1994 May 1; 218(2):278-83.

Kiefer H, Klee B, John E, Stierhof Y D, Jähnig F. Biosensors based on membrane transport proteins. Biosens Bioelectron. 1991; 6(3):233-7.

Svorc J, Miertus S, Barlíková A. Hybrid biosensor for the determination of lactose. Anal Chem. 1990 Aug. 1; 62(15):1628-31.

Pfeiffer D, Ralis E V, Makower A, Scheller F W. Amperometric bi-enzyme based biosensor for the detection of lactose-characterization and application. J Chem Technol Biotechnol. 1990; 49(3):255-65.

Heppel, L. A. and Porterfield, V. T. Enzymatic dehalogenation of certain brominated and chlorinated compounds. J. Biol. Chem. 176 (1948) 763-769.

Goldman, P., Milne, G. W. A. and Keister, D. B. Carbon-halogen bond cleavage. 3. Studies on bacterial halidohydrolases. *J. Biol. Chem.* 243 (1968) 428-434. [Medline UI: 68123008]

Motosugi, M., Esaki, N. and Soda, K. Preparation and properties of 2-halo acid dehydrogenase from *Pseudomonas putida*. Agric. Biol. Chem. 46 (1982) 837-838.

Goldman, P. The enzymatic cleavage of the carbon-fluorine bond in fluoroacetate. *J. Biol. Chem.* 240 (1965) 3434-3438.

Goldman, P. and Milne, G. W. A. Carbon-fluorine bond cleavage. II. Studies on the mechanism of the defluorination of fluoroacetate. *J. Biol. Chem.* 241 (1966) 5557-5559. [Medline UI: 67053221]

Chopra, I. J. and Teco, G. N. C. Characteristics of inner ring (3 or 5) monodeiodination of 3,5-diiodothyronine in rat liver: evidence suggesting marked similarities of inner and outer ring deiodinases for iodothyronines. *Endocrinology* 110 (1982) 89-97. [Medline UI: 82095045]

Goswani, A., Leonard, J. L. and Rosenberg, I. N. Inhibition by coumadin anticoagulants of enzymatic outer ring monodeiodination of iodothyronines. *Biochem. Biophys. Res. Commun.* 104 (1982) 1231-1238. [Medline UI: 82182305]

Smallridge, R. C., Burman, K. D., Ward, K. E., Wartofsky, L., Dimond, R. C., Wright, F. D. and Lathan, K. R. 3',5'-Diiodothyronine to 3'-monoiodothyronine conversion in the fed and fasted rat: enzyme characteristics and evidence for two distinct 5'-deiodinases. *Endocrinology* 108 (1981) 2336-2345. [Medline UI: 81188610]

Keuning, S., Janssen, D. B. and Witholt, B. Purification and characterization of hydrolytic haloalkane dehalogenase from *Xanthobacter autotrophicus* GJ10. *J. Bacteriol.* 163 (1985) 635-639. [Medline UI: 85261076]

Scholtz, R., Leisinger, T., Suter, F. and Cook, A. M. Characterization of 1-chlorohexane halidohydrolase, a dehalogenase of wide substrate range from an *Arthrobacter* sp. *J. Bacteriol.* 169 (1987) 5016-5021. [Medline UI: 88032819]

Yokota, T., Omori, T. and Kodama, T. Purification and properties of haloalkane dehalogenase from *Corynebacterium* sp. strain m15-3. *J. Bacteriol.* 169 (1987) 4049-4054. [Medline UI: 87307981]

Muller, R., Thiele, J., Klages, U. and Lingens, F. Incorporation of [18O]water into 4-hydroxybenzoic acid in the reaction of 4-chlorobenzoate dehalogenase from *Pseudomonas* sp. CBS 3. *Biochem. Biophys. Res. Commun.* 124 (1984) 178-182. [Medline UI: 85046491]

Chang, K. H., Liang, P. H., Beck, W., Scholten, J. D., Dunaway-Mariano, D. Isolation and characterization of the three polypeptide components of 4-chlorobenzoate dehalogenase from *Pseudomonas* sp. strain CBS-3. *Biochemistry* 31 (1992) 5605-5610. [Medline UI: 92304935]

Crooks, G. P., Copley, S. D. Purification and characterization of 4-chlorobenzoyl CoA dehalogenase from *Arthrobacter* sp. strain 4-CB1. *Biochemistry,* 33 (1994) 11645-11649. [Medline UI: 95001870]

de Souza, M. L., Wackett, L. P., Boundy-Mills, K. L., Mandelbaum, R. T. and Sadowsky, M. J. Cloning, characterization, and expression of a gene region from *Pseudomonas* sp. strain ADP involved in the dechlorination of atrazine. *Appl. Environ. Microbiol.* 61 (1995) 3373-3378. [Medline UI: 96035669]

de Souza, M. L., Sadowsky, M. J. and Wackett, L. P. Atrazine chlorohydrolase from *Pseudomonas* sp. strain ADP: gene sequence, enzyme purification, and protein characterization. *J. Bacteriol.* 178 (1996) 4894-4900. [Medline UI: 96326334]

Lipke, H. and Kearns, C. W. DDT dechlorinase. I. Isolation, chemical properties, and spectrophotometric assay. *J. Biol. Chem.* 234 (1959) 2123-2128.

Lipke, H. and Kearns, C. W. DDT dechlorinase. II. Substrate and cofactor specificity. *J. Biol. Chem.* 234 (1959) 2129-2132.

Moorefield, H. H. Purification of DDT-dehydrochlorinase from resistant houseflies. Contr. Boyce Thompson Inst. 18 (1956) 303-310.

Nagasawa, T., Ishii, T. and Yamada, H. Physiological comparison of D-cysteine desulfhydrase of *Escherichia coli* with 3-chloro-D-alanine dehydrochlorinase of *Pseudomonas putida* CR 1-1. *Arch. Microbiol.* 149 (1988) 413-416. [Medline UI: 88251237]

Yamada, H., Nagasawa, T., Ohkishi, H., Kawakami, B. and Tani, Y. Synthesis of D-cysteine from 3-chloro-D-alanine and hydrogen sulfide by 3-chloro-D-alanine hydrogen chloride-lyase (deaminating) of *Pseudomonas putida*. *Biochem. Biophys. Res. Commun.* 100 (1981) 1104-1110. [Medline UI: 81281807]

Kohler-Staub, D. and Leisinger, T. Dichloromethane dehalogenase of *Hyphomicrobium* sp. strain DM2. *J. Bacteriol.* 162 (1985) 676-681. [Medline UI: 85182487]

Moriguchi, M., Hoshino, S. and Hatanaka, S.-I. Dehalogenation and deamination of 1-2-amino-4-chloro-4-pentenoic acid by *Proteus mirabilis*. *Agric. Biol. Chem.* 51 (1987) 3295.

Kumagai, H., Suzuki, H., Shigematsu, H. and Tuchikura, T. S-Carboxymethylcysteine synthase from *Escherichia coli*. *Agric. Biol. Chem.* 53 (1989) 2481-2487.

Hayaishi, O. Direct oxygenation by O₂, oxygenases. In: Boyer, P. D., Lardy, H. and Myrbäck, K. (Eds.), *The Enzymes,* 2nd ed., vol. 8, Academic Press, New York, 1963, p. 353-371.

Junker, F., Field, J. A., Bangerter, F., Ramsteiner, K., Kohler, H.-P., Joannou, C. L., Mason, J. R., Leisinger, T. and Cook, A. M. Dioxygenation and spontaneous deamination of 2-aminobenzene sulphonic acid in *Alcaligenes* sp. strain 0-1 with subsequent meta ring cleavage and spontaneous desulphonation to 2-hydroxymuconic acid. *Biochem. J.* 300 (1994) 429-436.

Fujisawa, H. and Hayaishi, O. Protocatechuate 3,4-dioxygenase. I. Crystallization and characterization. *J. Biol. Chem.* 243 (1968) 2673-2681.

Adachi, K., Iwayama, Y., Tanioka, H. and Takeda, Y. Purification and properties of homogentisate oxygenase from *Pseudomonas fluorescens*. *Biochim. Biophys. Acta* 118 (1966) 88-97.

Hayaishi, O. and Sutton, W. B. Enzymatic oxygen fixation into acetate concomitant with the enzymatic decarboxylation of L-lactate. *J. Am. Chem. Soc.* 79 (1957) 4809-4810.

Renganathan, V. Possible involvement of toluene-2,3-dioxygenase in defluorination of 3-fluoro-substituted benzenes by toluene-degrading *Pseudomonas* sp. strain T-12. *Appl. Exp. Microbiol.* 55 (1989) 330-334.

Ensley, B. D. and Gibson, D. T. Naphthalene dioxygenase: purification and properties of a terminal oxygenase component. *J. Bacteriol.* 155 (1983) 505-511.

Fetzner, S., Mueller, R. and Lingens, F. Degradation of 2-chlorobenzoate by *Pseudomonas cepacia* 2CBS. *Biol. Chem. Hoppe-Seyler* 370 (1989) 1173-1182.

Suzuki, K., Takemori, S. and Katagiri, M. Mechanism of the salicylate hydroxylase reaction. IV. Fluorimetric analysis of the complex formation. *Biochim. Biophys. Acta* 191 (1969) 77-85.

Hosokawa, K. and Stanier, R. Y. Crystallization and properties of p-hydroxybenzoate hydroxylase from *Pseudomonas putida*. *J. Biol. Chem.* 241 (1966) 2453-2460.

Nakagawa, H. and Takeda, Y. Phenol hydroxylase. *Biochim. Biophys. Acta* 62 (1962) 423-426.

Ziegler, D. M. and Pettit, F. H. Microsomal oxidases. I. The isolation and dialkylarylamine oxygenase activity of pork liver microsomes. *Biochemistry* 5 (1966) 2932-2938.

Colby, J. Stirling, D. I. and Dalton, H. The soluble methane mono-oxygenase of *Methylococcus capsulatus* (Bath). Its ability to oxygenate n-alkanes, n-alkenes, ethers, and alicyclic, aromatic and heterocyclic compounds. *Biochem. J.* 165 (1977) 395-402.

Schenk, T., Müller, R., Mörsberger, F., Otto, M. K. and Lingens, F. Enzymatic dehalogenation of pentachlorophenol by extracts from *Arthrobacter* sp. strain ATCC 33790. *J. Bacteriol.* 171 (1989) 5487-5491.

Cardini, G. and Jurtshuk, P. The enzymatic hydroxylation of n-octane by *Corynebacterium* sp. strain 7E1C. *J. Biol. Chem.* 245 (1970) 2789-2796.

Augusteyn, R. C., de Jersey, J., Webb, E. C. and Zerner, B. On the homology of the active-site peptides of liver carboxylesterases. *Biochim. Biophys. Acta* 171 (1969) 128-137.

Dodgson, K. S., Spencer, B. and Williams, K. Studies on sulphatases. 13. The hydrolysis of substituted phenyl sulphates by the arylsulphatase of *Alcaligenes metacaligenes*. *Biochem. J.* 64 (1956) 216-221.

Aldridge, W. N. Serum esterases. I. Two types of esterase (A and B) hydrolysing p-nitrophenyl acetate, propionate and butyrate and a method for their determination. *Biochem. J.* 53 (1953) 110-117.

Augustinsson, K.-B. and Heimburger, G. Enzymatic hydrolysis of organophosphorus compounds. I. Occurrence of enzymes hydrolysing dimethyl-amido-ethoxy-phosphoryl cyanide (Tabun). *Acta Chem. Scand.* 8 (1954) 753-761.

Cardy, D. L. N., V. Laidler, G. P. C. Salmond, and J. C. Murrell, "Molecular Analysis of the Methane Monooxygenase (MMO) Gene Cluster of *Methylosinus trichosporium* OB3b," *Molecular Microbiology*, 1991. 5(2): pp. 335-342.

Stainthorpe, A. C., V. Lees, G. P. C. Salmond, H. Dalton, and J. C. Murrell, "The Methane Monooxygenase Gene Cluster of *Methylococcus capsulatus* (Bath)," *Gene*, 1990. 91: pp. 27-34.

Rosenzwieg, A. C., P. Nordlund, P. M. Takahara, C. A. Frederick, and S. J. Lippard, "Geometry of the Soluble Methane Monoxygenase Catalytic Diiron Center in Two Oxidation States," *Chemistry and Biology*, 1995. 2(6): pp. 409-418.

Shields, M. S. and S. C. Francesconi, *Microbial Degradation of Trichloroethylene, Dichloroethylene, and Aromatic Pollutants*, in U.S. Pat. No. 5,543,317. 1996.

Bertoni, G., F. Bolognese, E. Galli, and P. Barbieri, "Cloning of the Genes for and Characterization of the Early Stages of Toluene and o-Xylene Catabolism in *Pseudomonas stutzeri* OX1," *Applied and Environmental Microbiology*, 1996, 62(10): pp. 3704-3711

Bertoni, G., M. Martino, E. Galli, and P. Barbieri, "Analysis of the Gene Cluster Encoding Toluene/o-Xylene Monoxygenase from *Pseudomonas stutzeri* OX1," *Applied and Environmental Microbiology*, 1998. 64(10): pp. 3626-3632.

Pikus, J. D., J. M. Studts, C. Achim, K. E. Kauffmann, E. Munck, R. J. Steffan, K. McClay, and B. G. Fox, "Recombinant Toluene-4-Monoxygenase: Catalytic and Mossbauer Studies of the Purified Diiron and Rieski Components of a Four-Protein Complex," *Biochemistry*, 1996. 35: pp. 9106-9119; Yen, K.-M., "Construction of Cloning Cartridges for Development of Expression Vectors in Gram-Negative Bacteria," *J. Bacteria.*, 1991. 173(17): pp. 5328-5335.

Newman, 1995; McClay, K., B. G. Fox, and R. J. Steffan, "Chloroform Mineralization by Toluene-Oxidizing Bacteria," *Applied and Environmental Microbiology*, 1996. 62(8): pp. 2716-2722.

Byrne, A. M., J. J. Kukor, and R. H. Olsen, "Sequence Analysis of the Gene Cluster Encoding Toluene-3-monooxygenase from *Pseudomonas pickettii* PK01," *Gene*, 1995. 154: pp. 65-70.

Nordlund, I., J. Powlowski, and V. Shingler, "Complete nucleotide sequence and polypeptide analysis of multicomponent phenol hydroxylase from *Pseudomonas* sp. strain CF600," *Journal of Bacteriology*, 1990. 172: pp. 6826-6833.

Stoica, L. and Ludwig, R. and Haltrich, D. and Gorton, L., Third-generation biosensor for lactose based on newly discovered cellobiose dehydrogenase, Analytical chemistry, vol. 78, no. 2, pp. 393-398, 2006.

Sharma, S. K. and Singhal, R. and Malhotra, B D and Sehgal, N. and Kumar, A., Lactose biosensor based on Langmuir-Blodgett films of poly 3-hexyl thiophene, Biosensors and Bioelectronics, vol. 20, no. 3, pp. 651-657, 2004.

Ferreira, L S and Trierweiler, J O and De Souza Jr, M B and Folly, R O M, A lactose fia-biosensor system for monitoring and process control, Brazilian Journal of Chemical Engineering, vol. 21, no. 2, pp. 307-315, 2004.

Marrakchi, M. and Dzyadevych, S. V. and Lagarde, F. and Martelet, C. and Jaffrezic-Renault, N., Conductometric biosensor based on glucose oxidase and beta-galactosidase for specific lactose determination in milk, Materials Science and Engineering: C, vol. 28, nos. 5-6, pp. 872-875, 2008.

Eshkenazi, I. and Maltz, E. and Zion, B. and Rishpon, J., A Three-Cascaded-Enzymes Biosensor to Determine Lactose Concentration in Raw Milk, Journal of dairy science, vol. 83, no. 9, pp. 1939-1945, 2000.

Liu, H. and Li, H. and Ying, T. and Sun, K. and Qin, Y. and Qi, D., Amperometric biosensor sensitive to glucose and lactose based on co-immobilization of ferrocene, glucose oxidase, beta-galactosidase and mutarotase in beta-cyclodextrin polymer, Analytica Chimica Acta, vol. 358, no. 2, pp. 137-144, 1998.

Tkac, J. and Sturdik, E. and Gemeiner, P., Novel glucose non-interference biosensor for lactose detection based on galactose oxidase-peroxidase with and without co-immobilised [small beta]-galactosidase, Analyst, vol. 125, no. 7, pp. 1285-1289, 2000.

Svorc, J. and Miertus, S. and Barlikova, A., Hybrid biosensor for the determination of lactose, Analytical chemistry, vol. 62, no. 15, pp. 1628-1631, 1990.

Pfeiffer, D. and Ralis, E. V. and Makower, A. and Scheller, F. W., Amperometric Bi-enzyme based biosensor for the detection of lactose—characterization and application, Journal of Chemical Technology and Biotechnology, vol. 49, no. 3, pp. 255-265, 1990.

Pilloton, R. and Mascini, M., Flow analysis of lactose and glucose in milk with an improved electrochemical biosensor, Food chemistry, vol. 36, no. 3, pp. 213-222, 1990.

Jenkins, D. M. and Delwiche, M. J., Adaptation of a manometric biosensor to measure glucose and lactose, Biosensors and Bioelectronics, vol. 18, no. 1, pp. 101-107, 2003.

Frreira, L S and Souza Jr, M B and Trierweiler, J O and Hitzmann, B. and Folly, R O M, Analysis of experimental biosensor/FIA lactose measurements, Brazilian Journal of Chemical Engineering, vol. 20, no. 1, pp. 7-13, 2003.

Ottenbacher, D. and Jahnig, F. and Gopel, W., A prototype biosensor based on transport proteins: Electrical transducers applied to lactose permease, Sensors and Actuators B: Chemical, vol. 13, nos. 1-3, pp. 173-175, 1993.

Loechel, C. and Chemnitius, G. C. and Borchardt, M. and Cammann, K., Amperometric bi-enzyme based biosensor for the determination of lactose with an extended linear range, Zeitschrift Lebensmitteluntersuchung und-Forschung A., vol. 207, no. 5, pp. 381-385, 1998.

Goktug, T. and Sezginturk, M. K. and Dinckaya, E., Glucose oxidase-[beta]-galactosidase hybrid biosensor based on glassy carbon electrode modified with mercury for lactose determination, Analytica chimica acta, vol. 551, nos. 1-2, pp. 51-56, 2005.

Yang, W. and Pang, P. and Gao, X. and Cai, Q. and Zeng, K. and Grimes, C. A., Detection of lactose in milk samples using a wireless multi-enzyme biosensor, Sensor Letters, vol. 5, no. 2, pp. 405-410, 2007.

Jturdk, E. and Gemeiner, P., Novel glucose non-interference biosensor for lactose detection based on galactose oxidase-peroxidase with and without co-immobilised beta-galactosidase, Analyst, vol. 125, no. 7, pp. 1285-1289, 2000

Louren, R J M and Serralheiro, M L M and Rebelo, M J F, Development of a new amperometric biosensor for lactose determination, Portugaliae Electrochimica Acta, vol. 21, no. 2, pp. 171-177, 2003.

Pyeshkova, V M and Saiapina, O Y and Soldatkin, O O and Kukla, O L and Dzyadevych, S V, Enzyme conductometric biosensor for determination of lactose, Biotechnology, pp. 76-84, 2008

Fritzen, M. and Schuhmann, W. and Lengeier, J W and Schmidt, H. L., Immobilized transport mutants of bacterial cells in biosensor arrays. Improved selectivity for the simultaneous determination of glucose and lactose, Progress in Biotechnology, vol. 11, pp. 821-827, 1996.

Svitel, J. and Curilla, O. and Tkac, J., Microbial cell-based biosensor for sensing glucose, sucrose or lactose, Biotechnology and applied biochemistry, vol. 27, no. 2, pp. 153-158, 1998.

Lu, E. and Sungur, S, and Yildiz, Y., Development of lactose biosensor based on beta-galactosidase and glucose oxidase immobilized into gelatin, Journal of Macromolecular Science, Part A, vol. 43, no. 3, pp. 525-533, 2006.

Lu, E. and Sungur, S, and Yildiz, Y., Development of Lactose Biosensor Based on Galactosidase and Glucose Oxidase Immobilized into Gelatin, Journal of Macromolecular Science-Part A: Pure and Applied Chemistry, vol. 43, no. 3, pp. 525-534, 2006.

Tkac, J. and Sturdik, E. and Gemeiner, P., Full Papers-Sensors-Novel glucose non-interference biosensor for lactose detection based on galactose oxidase-peroxidase with and without co-immobilised b-galactosidase, Analyst-Letchworth, 125, no. 7, 1285-1290, 2000.

Yang, C. and Zhang, Z. and Shi, Z. and Xue, P. and Chang, P. and Yan, R., Application of a novel co-enzyme reactor in chemiluminescence flow-through biosensor for determination of lactose, Talanta, 82, no. 1, 319-324, 2010.

Tkac, J. and Svitel, J., Bulletin Potravinarskeho Vyskumu (Slovak Republic); Determination of glucose and lactose in milk by a microbial biosensor; Stanovenie glukozy a laktozy v mlieku mikrobialnym sensorom, Bulletin of Food Research, 1997.

Park, I S and Kim, J H and Noh, B S and Kim, T J, Simultaneous determination of lactose and lactic acid in yoghurt by biosensor using dual cathode electrode, Korean Journal of Biotechnology and Bioengineering, Korea Republic, 1997.

C. Müller, F. Schubert and T. Scheper, Multicomponent fiberoptical biosensor for use in hemodialysis monitoring, SPIE Proc., Vol. 2131, pp. 555-562, Biomedical Fiber Optic Instrumentation, Los Angeles, Calif., USA, 1994.

Liu, H. and Ying, T. and Sun, K. and Li, H. and Qi, D., Reagentless amperometric biosensors highly sensitive to hydrogen peroxide, glucose and lactose based on N-methyl phenazine methosulfate incorporated in a Nafion film as an electron transfer mediator between horseradish peroxidase and an electrode, Analytica chimica acta, vol. 344, no. 3, pp. 187-199, 1997.

What is claimed:

1. A biosensing system that measures lactose concentration in a solution, said biosensing system comprising:
an optode comprising an optical fiber having a first tip and a second tip,
a luminescent transducer layer covering said first tip,
a biocomponent layer covering said luminescent transducer layer,
said biocomponent layer comprising at least one biocomponent that catalyzes a reaction with lactose in said solution, wherein
said at least one biocomponent is immobilized within said biocomponent layer using a hydrogel or polymer matrix,
a porous membrane covering said biocomponent layer, wherein said porous membrane provides a mass transfer resistance between said biocomponent layer and said solution,
a photon-detection device coupled to said second tip, wherein the photon-detection device is configured to detect photons emitted from the luminescent transducer layer through the optical fiber, and
a signal processing system coupled to said photon-detection device.

2. The biosensing system of claim 1 whereby said lactose concentration in said solution, the depth of said biocomponent layer, the depth of said porous membrane, the diffusion coefficient of lactose in said porous membrane, and the $K_M$ and $V_{max}$ of said catalytic reaction between said biocomponent and lactose are selected such that Da is greater than the value of $1-\beta$ and the quotient between $Da^2$ and $4\beta$ is from about 10 to at least 1000,
wherein $V_{max}$ is the maximum reaction rate of said biocomponent with lactose under saturating lactose concentrations, and
wherein $K_M$ is the lactose concentration at which the reaction rate of said biocomponent and lactose is half of $V_{max}$, and
wherein $\beta$ is the lactose concentration in said solution divided by said $K_M$ of said biocomponent for lactose, and
wherein Da is a dimensionless Damköhler number, and
wherein Da is $(h_e V_{max} h_p)/(D_p K_M)$, and
wherein $h_e$ is the thickness of said biocomponent layer, and
wherein $h_p$ is the thickness of said porous membrane, and
wherein $D_p$ is the diffusion coefficient of lactose in said porous membrane.

3. The biosensing system of claim 1 wherein said luminescent transducer layer contains a luminescent agent that is selected from the group consisting of
a fluorescent agent,
a phosphorescent agent,
a bioluminescent agent, or
a chemiluminescent agent.

4. The biosensing system of claim 1 wherein said luminescent transducer layer contains a luminescent agent that is selected from the group consisting of:
trisodium 8-hydroxy-1,3,6-trisulphonate, fluoro (8-anilino-l-naphthalene sulphonate), tris(bipyridine)ruthenium(II) complex, Tris(4,7-diphenyl-1,10-phenanthroline)Ru(II) (RuDPP), ruthenium complexes, and acridinium- and quinidinium-based reagents, fluorescein, fluoresceinamine, or a fluorescein containing compound.

5. The biosensing system of claim 1 wherein said biocomponent layer comprises a biocomponent selected from the group consisting of at least one enzyme from Enzyme Commission numbers 1.1.3, 1.2.3, 1.3.3, 1.4.3, 1.5.3, 1.6.3, 1.7.3, 1.8.3, 1.9.3, 1.10.3, 1.16.3, 1.17.3, 1.21.3, and 3.2.1.23.

6. The biosensing system of claim 1 wherein said polymer matrix comprises one or more of polyacrylamide, polystyrene, polymethacrylate, polyvinylalcohol and polyurethane, and wherein said biocomponent is entrapped within said polymer matrix.

7. The biosensing system of claim 6 wherein said biocomponent is bound to said matrix layer through adding crosslinking agents to said biocomponent entrapped within said matrix layer, and
wherein said crosslinking agents are selected from the group consisting of glutaraldehyde, hexamethylene diisocyanate and 1,5-dinitro-2,4-difluorobenzene, polyethyleneimine, hexamethylenediamine and formaldehyde.

8. The biosensing system of claim 1 wherein said luminescent transducer layer is bound in a layer of molecules bound to the first tip of said optical fiber, said layer of molecules is selected from the group consisting of cellulose, cellulose derivatives, silica, glass, dextran, starch, agarose, porous silica, chitin and chitosan.

9. The biosensing system of claim 1, said porous membrane is polycarbonate having a pore size of from about 0.005 µm to about 0.025 µm.

10. The biosensing system of claim 9, said porous membrane comprises a coating of polyurethane.

11. The biosensing system of claim 1 wherein said biocomponent comprises beta-galactosidase and glucose oxidase and wherein luminescence of said luminescent transducer layer is at least partially quenched with oxygen.

12. The biosensing system of claim 11 wherein said biocomponent further comprises catalase.

13. The biosensing system of claim 1 wherein said biocomponent comprises beta-galactosidase and galactose oxidase and wherein luminescence of said luminescent transducer layer is at least partially quenched with oxygen.

14. The biosensing system of claim 13 wherein said biocomponent further comprises catalase.

15. The biosensing system of claim 1 wherein said biocomponent is carbohydrate oxidase and wherein luminescence of said luminescent transducer layer is at least partially quenched with oxygen.

16. The biosensing system of claim 1 wherein said biocomponent further comprises catalase.

17. The biosensing system of claim 1 wherein said biocomponent is cellobiose dehydrogenase and wherein luminescence of said luminescent transducer layer interacts with protons.

18. The biosensing system of claim 1 wherein said biocomponent comprises beta-galactosidase and hexose oxidase and wherein luminescence of said luminescent transducer layer is at least partially quenched with oxygen.

19. The biosensing system of claim 18 wherein said biocomponent further comprises catalase.

20. The biosensing system of claim 1, wherein said hydrogel comprises one or more of algal polysaccharides, agarose, alginate, gelatin, collagen, pectin, poly(carbamoyl) sulfonate, locust bean gum, and gellan, and wherein said biocomponent is entrapped within said hydrogel.

21. The biosensing system of claim 1, wherein said biocomponent layer further comprises one or more of a gel-hardening agent and a stabilizing agent.

22. The biosensing system of claim 21, wherein said one or more of a gel-hardening agent and a stabilizing agent comprises one or more of glutaraldehyde, polyethyleneimine, hexamethylenediamine and formaldehyde.

23. The biosensing system of claim 1, wherein said porous membrane enables said biosensing system to measure lactose in said solution at concentrations up to and including 20 mM.

24. The biosensing system of claim 1, wherein said porous membrane enables said biosensing system to measure lactose in said solution at concentrations up to and including 100 mM.

25. The biosensing system of claim 1, wherein said luminescent transducer layer comprises one or more fluorophores capable of interacting with protons.

* * * * *